US012098361B2

(12) United States Patent
Hess et al.

(10) Patent No.: US 12,098,361 B2
(45) Date of Patent: Sep. 24, 2024

(54) ATTENUATED *HISTOMONAS MELEAGRIDIS* STRAIN AND VACCINE

(71) Applicant: VETERINÄRMEDIZINISCHE UNIVERSITÄT WIEN, Vienna (AT)

(72) Inventors: Michael Hess, Vienna (AT); Ivana Bilic, Vienna (AT); Nicola Palmieri, Vienna (AT)

(73) Assignee: VETERINÄRMEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 17/851,692

(22) Filed: Jun. 28, 2022

(65) Prior Publication Data

US 2023/0045943 A1 Feb. 16, 2023

(30) Foreign Application Priority Data

Jun. 29, 2021 (EP) .................................... 21182469

(51) Int. Cl.
*C12N 1/10* (2006.01)
*A61K 39/002* (2006.01)
*A61P 33/04* (2006.01)
*A61K 39/00* (2006.01)

(52) U.S. Cl.
CPC .............. *C12N 1/10* (2013.01); *A61K 39/002* (2013.01); *A61P 33/04* (2018.01); *A61K 2039/522* (2013.01)

(58) Field of Classification Search
None
See application file for complete search history.

(56) References Cited

FOREIGN PATENT DOCUMENTS

WO WO 2014/006018 A 1/2014

OTHER PUBLICATIONS

Hess, M., et al., "Cloned *Histomonas meleagridis* passaged in vitro resulted in reduced pathogenicity and is capable of protecting turkeys from histomonosis", Vaccine, (2008), pp. 4187-4193, vol. 26.

European Search Report dated Jan. 14, 2022 for European Application No. 21182469.3-1118.

*Primary Examiner* — Oluwatosin A Ogunbiyi

(74) *Attorney, Agent, or Firm* — Greer, Burns & Crain, Ltd

(57) ABSTRACT

A *Histomonas meleagridis* strain having at least one of the following attenuating features (a) an inactivation of a gene, wherein the gene has the sequence identified by SEQ ID NO: 1 or a sequence with at least 90% sequence identity thereto, (b) an inactivation of a gene, wherein the gene has the sequence identified by SEQ ID NO: 2 or a sequence with at least 90% sequence identity thereto, (c) a truncating mutation in the coding sequence of a gene, wherein the gene has the unmutated coding sequence identified by SEQ ID NO: 3 or an unmutated coding sequence with at least 95% sequence identity thereto, and (d) a truncating mutation in the coding sequence of a gene, wherein the gene has the unmutated coding sequence identified by SEQ ID NO: 4 or an unmutated coding sequence with at least 95% sequence identity thereto. An anti-histomonosis vaccine containing the strain.

19 Claims, 17 Drawing Sheets

Specification includes a Sequence Listing.

(a)

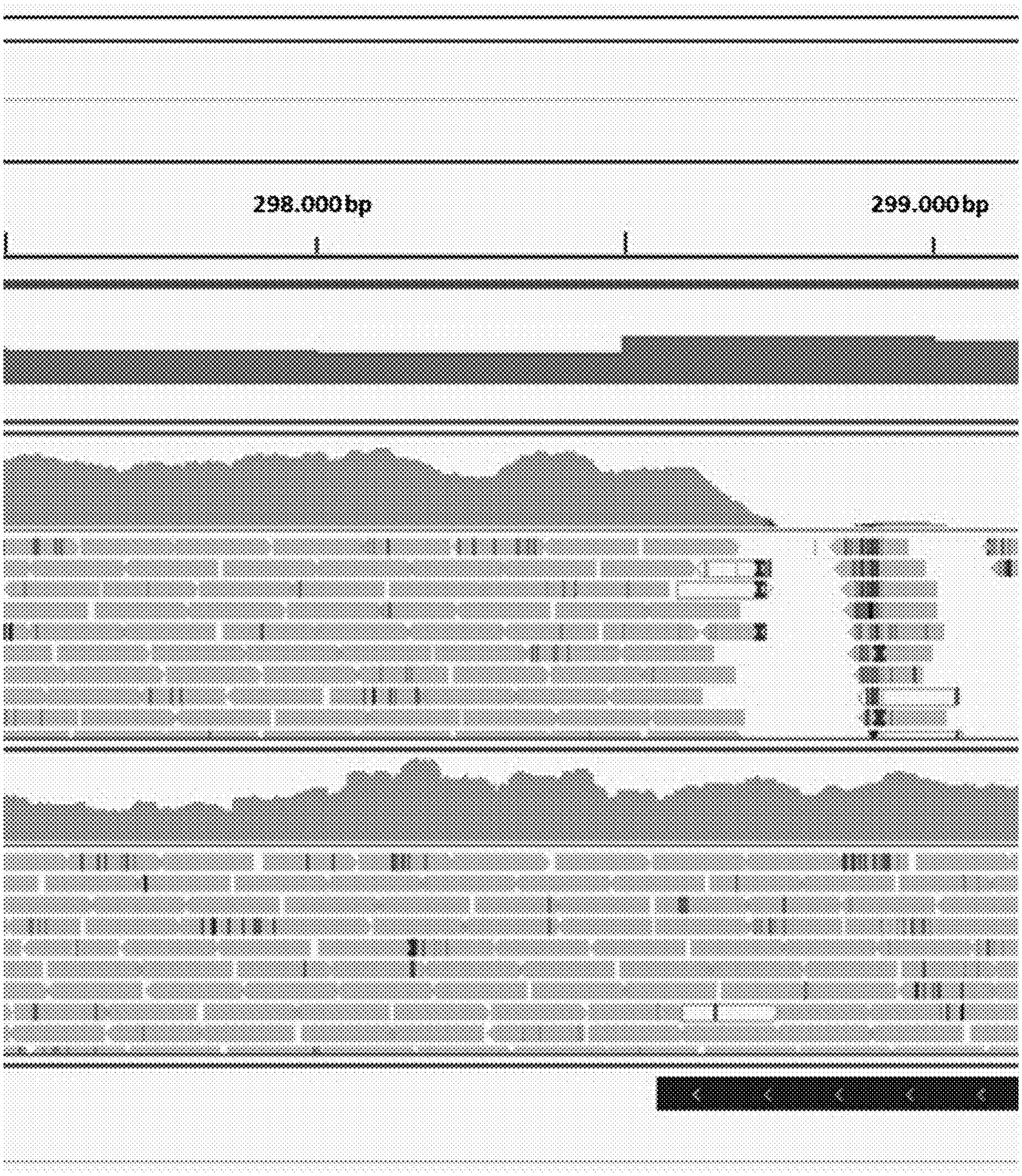
Fig. 2 (ctd)

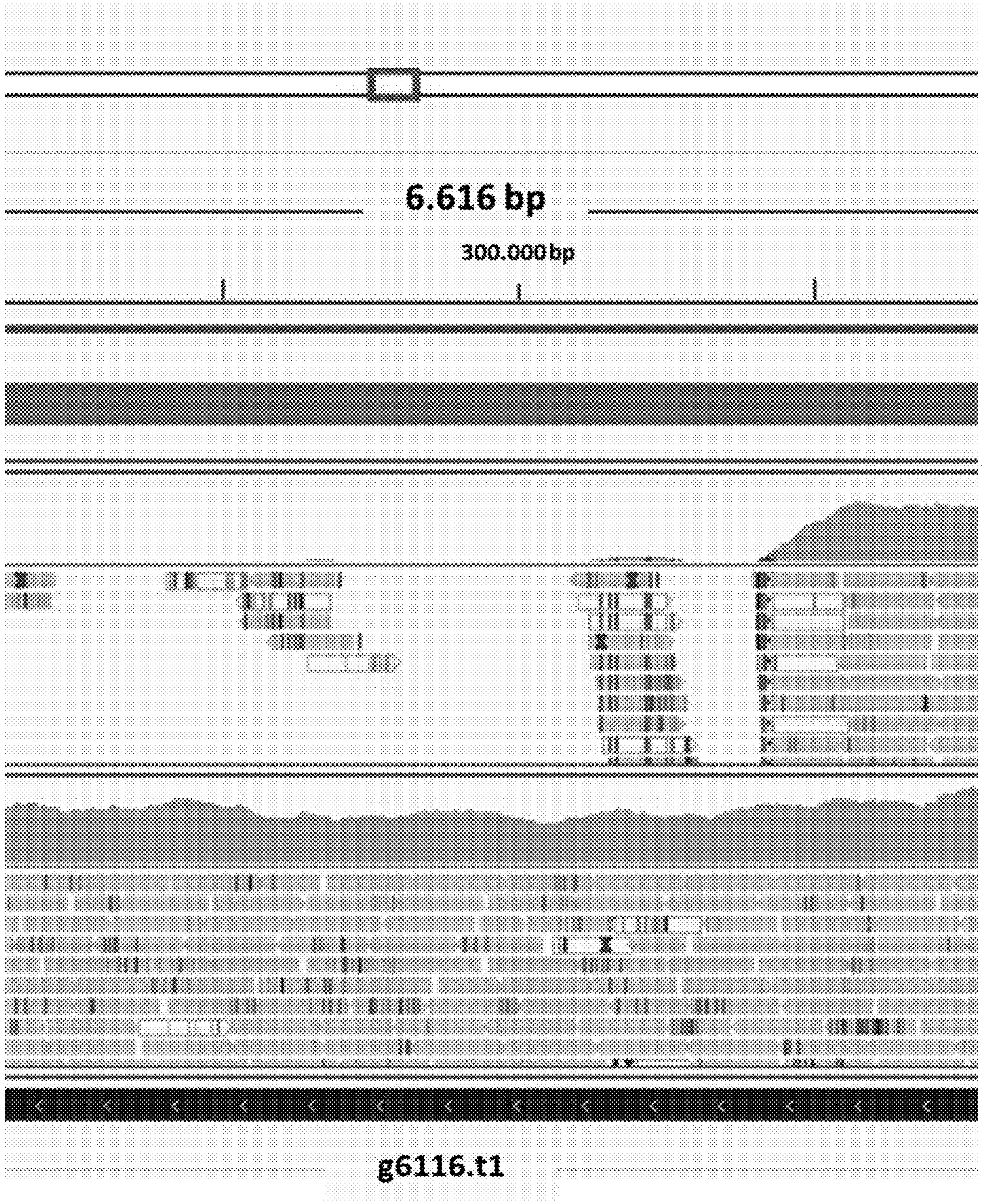
Fig. 2 (ctd)

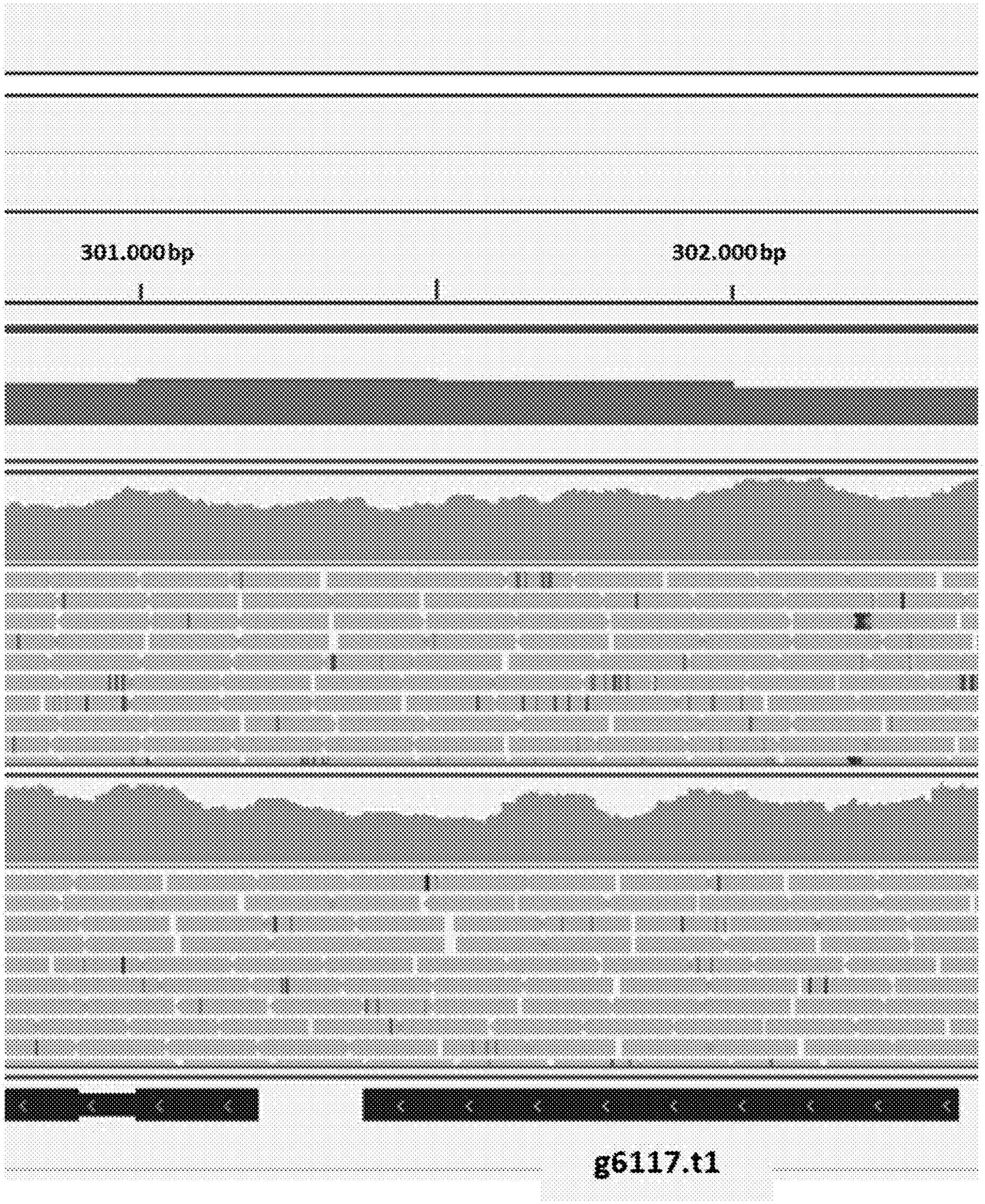
Fig. 2 (ctd)

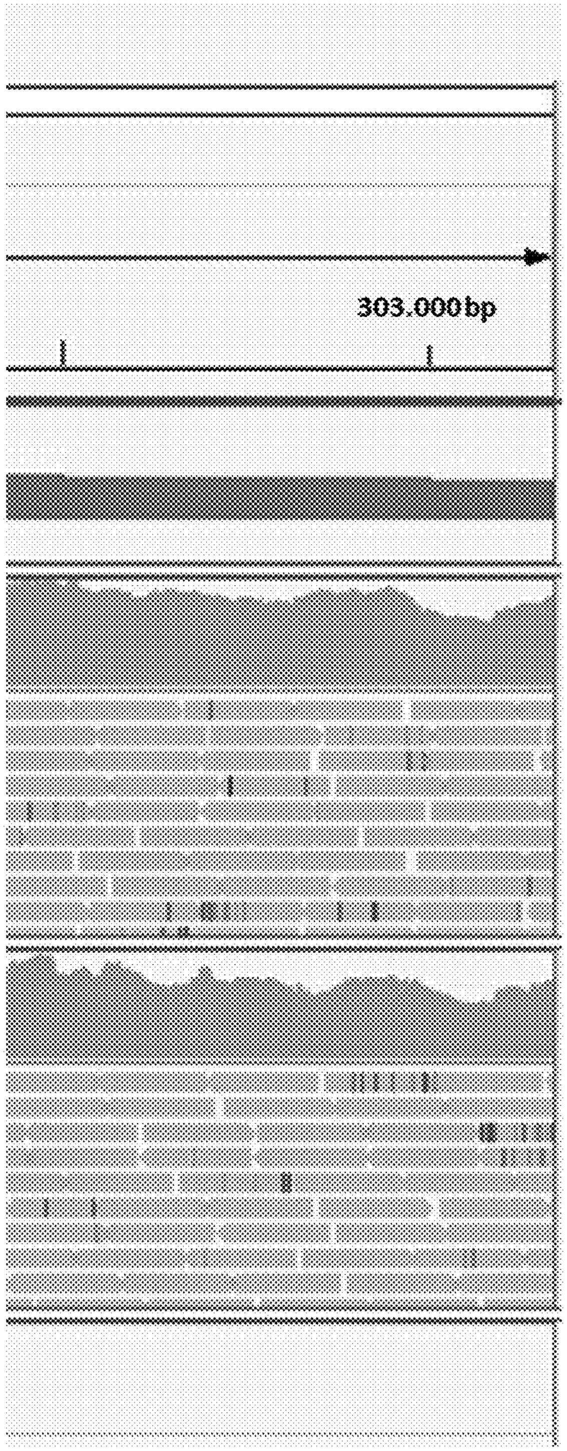
Fig. 2 (ctd)

(b)
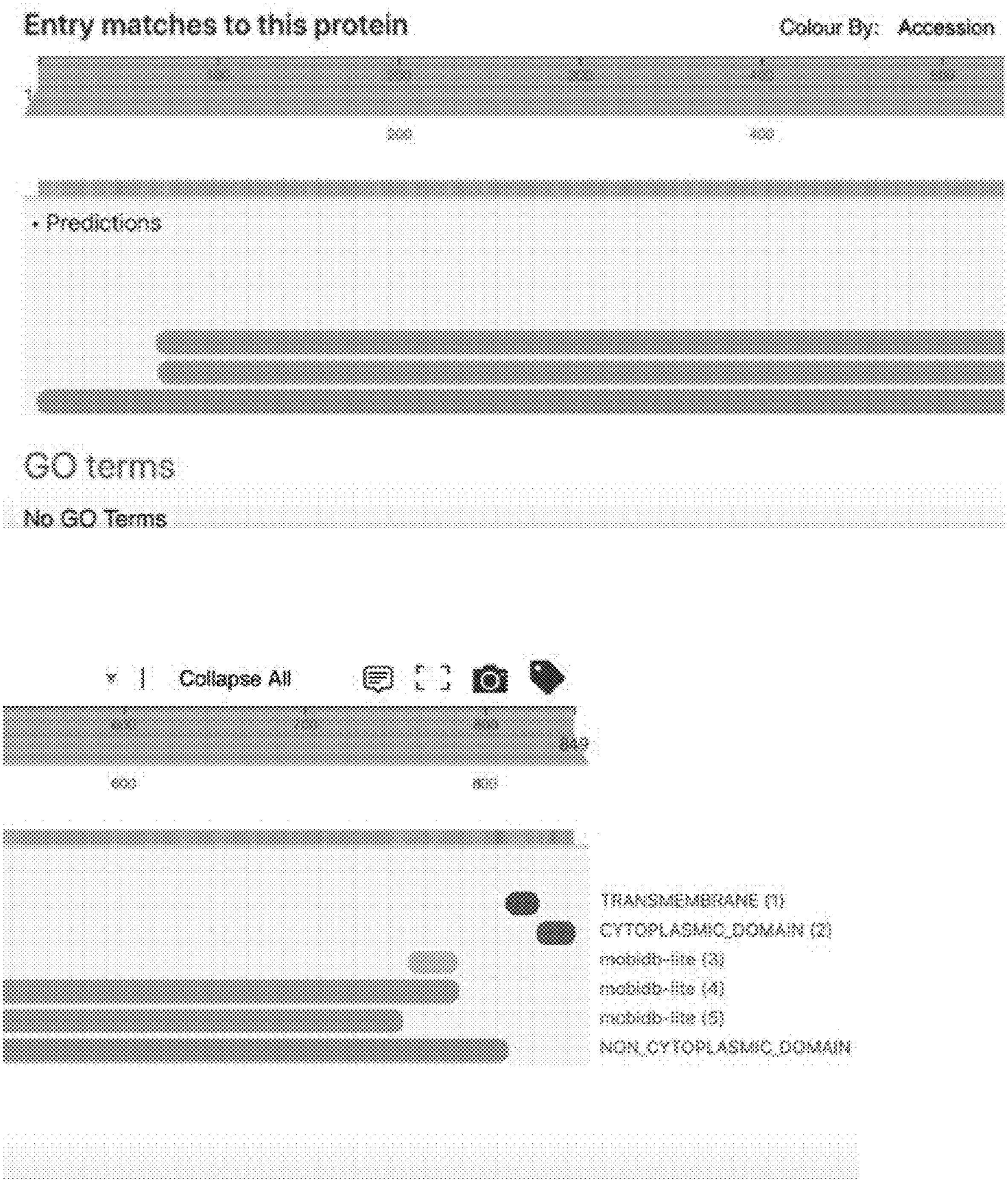
Fig. 2 (ctd)

(a)

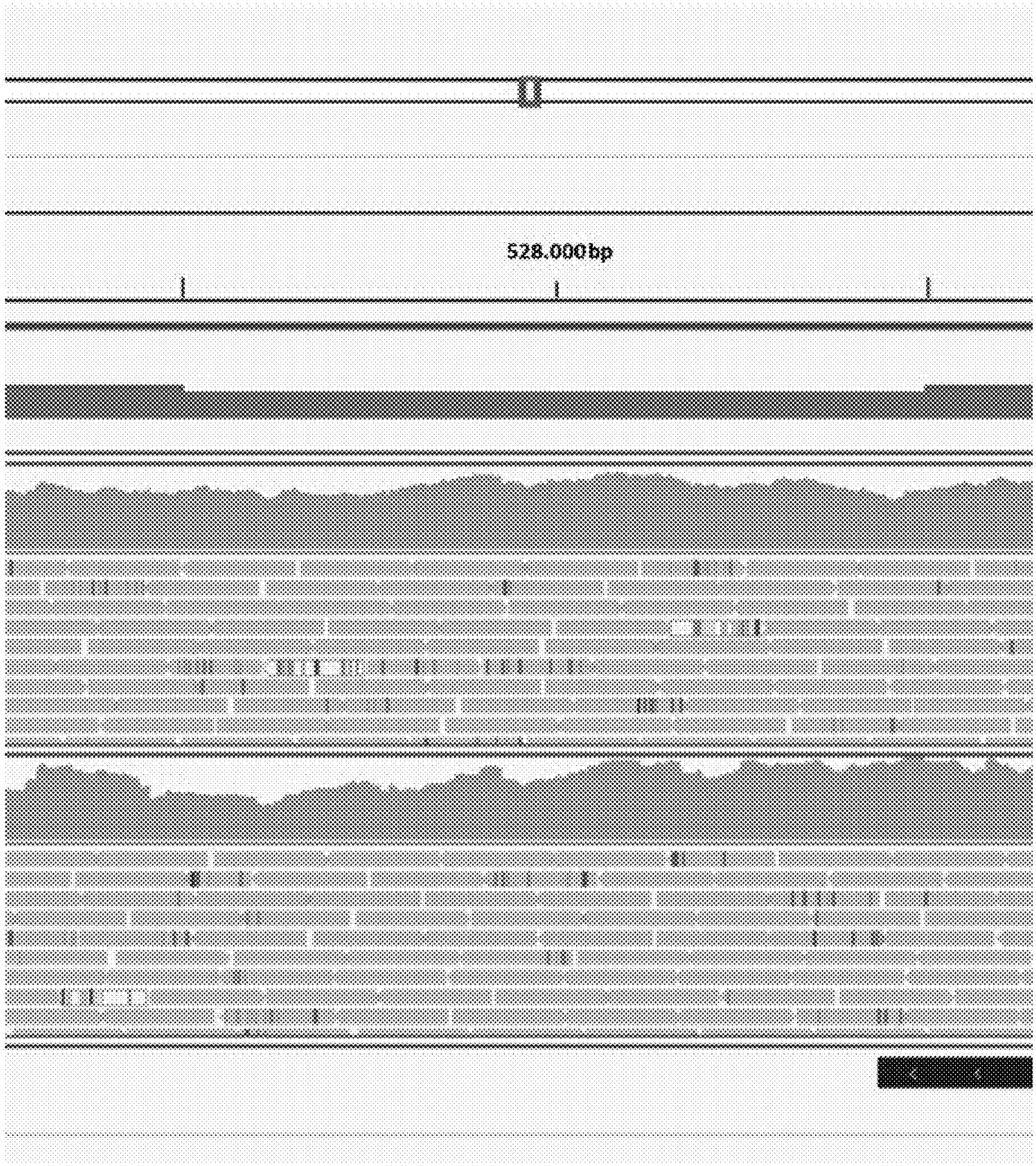
Fig. 3 (ctd)

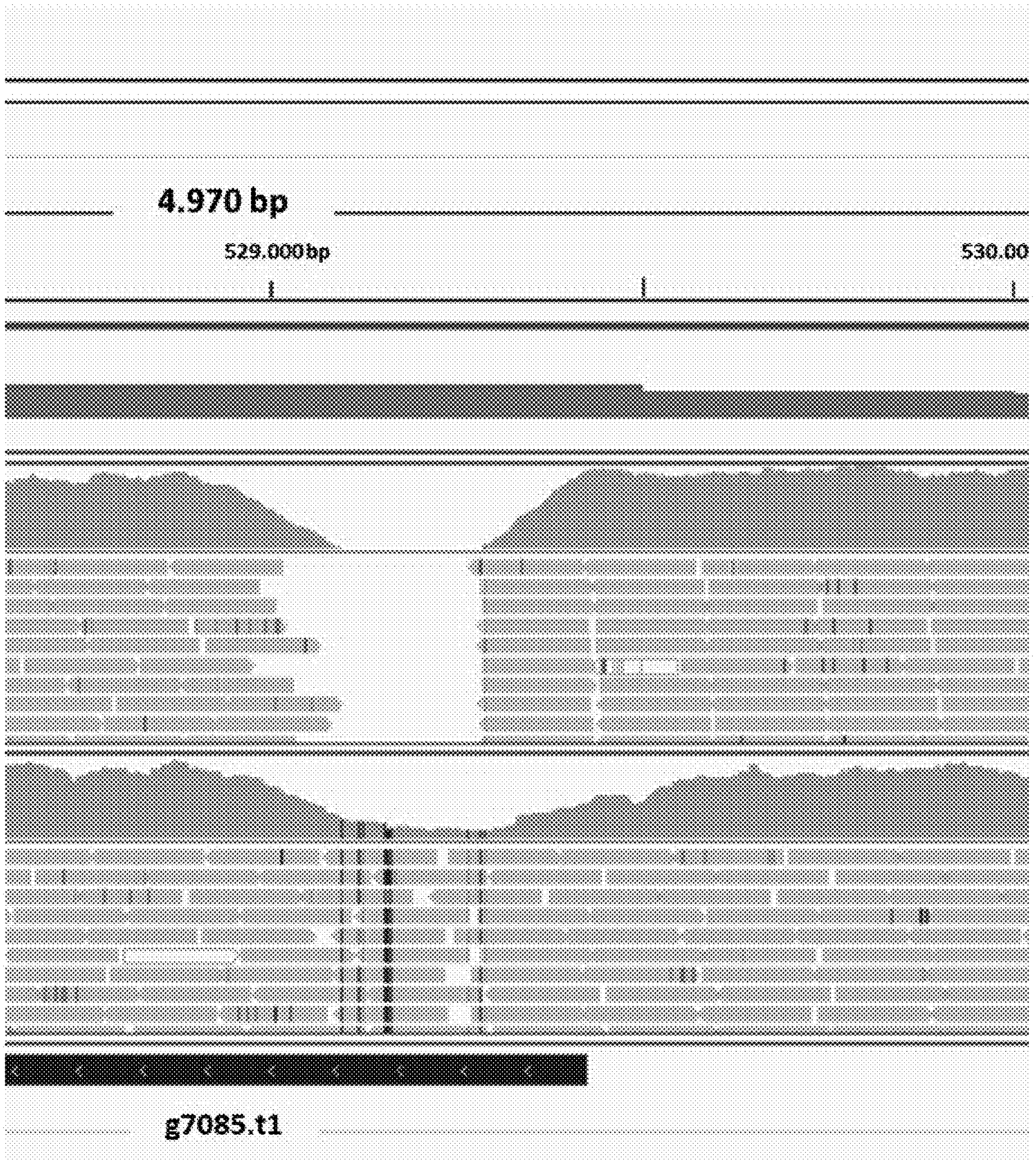
Fig. 3 (ctd)

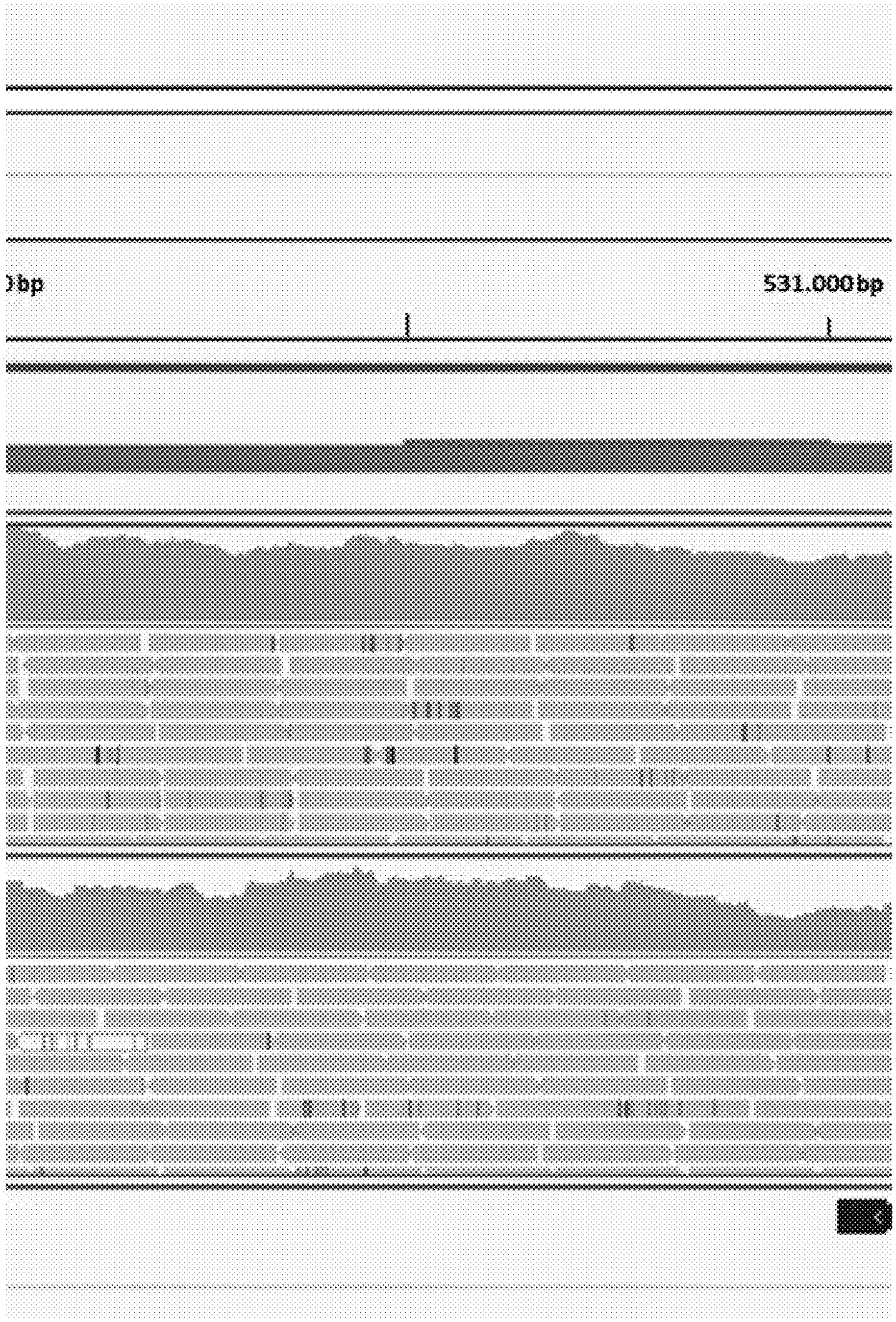
Fig. 3 (ctd)

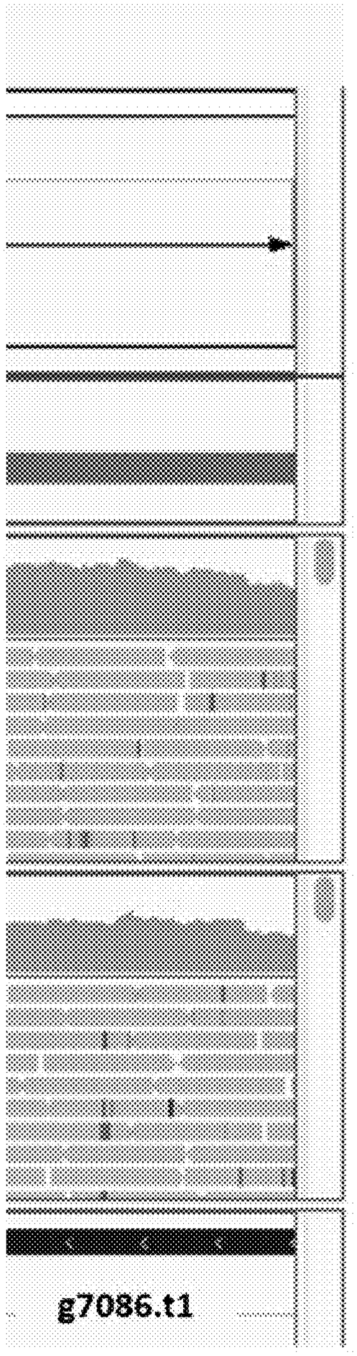
Fig. 3 (ctd)

(b)

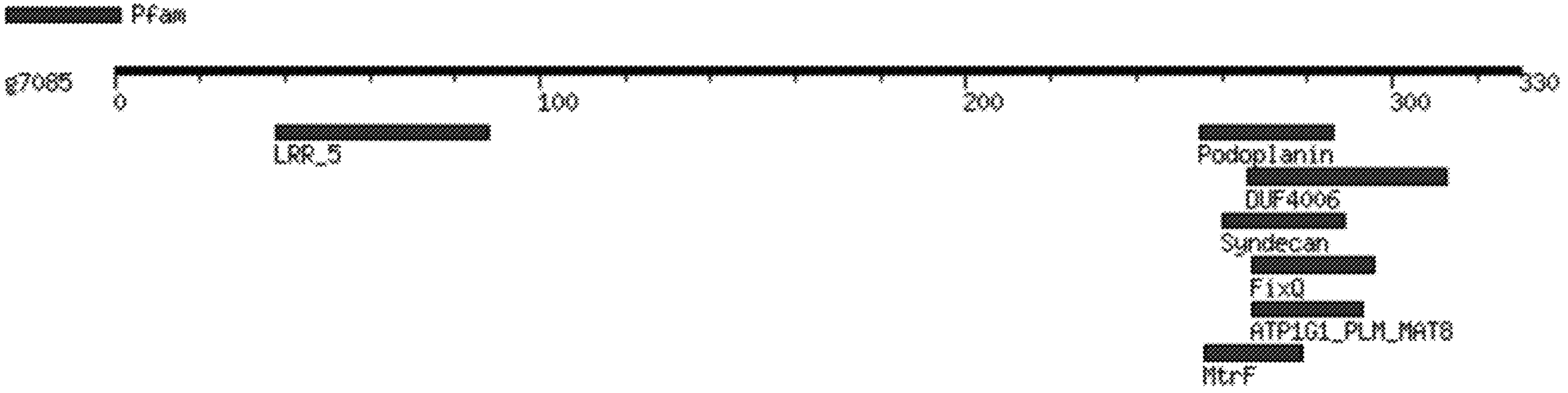

Pfam (7 motifs)

| Pfam | Position(Independent E-value) | | Description |
|---|---|---|---|
| LRR_5 | 38..88(6.1e-08) | Detail | PF13306, BspA type Leucine rich repeat region (6 copies) |
| Podoplanin | 255..286(0.0027) | Detail | PF05808, Podoplanin |
| DUF4006 | 266..313(0.065) | Detail | PF13179, Family of unknown function (DUF4006) |
| Syndecan | 260..289(0.18) | Detail | PF01034, Syndecan domain |
| FixQ | 267..296(0.28) | Detail | PF05545, Cbb3-type cytochrome oxidase component FixQ |
| ATP1G1_PLM_MAT8 | 267..293(0.54) | Detail | PF02038, ATP1G1/PLM/MAT8 family |
| MtrF | 256..279(0.77) | Detail | PF09472, Tetrahydromethanopterin S-methyltransferase, F subunit (MtrF) |

Fig. 3 (ctd)

(c)
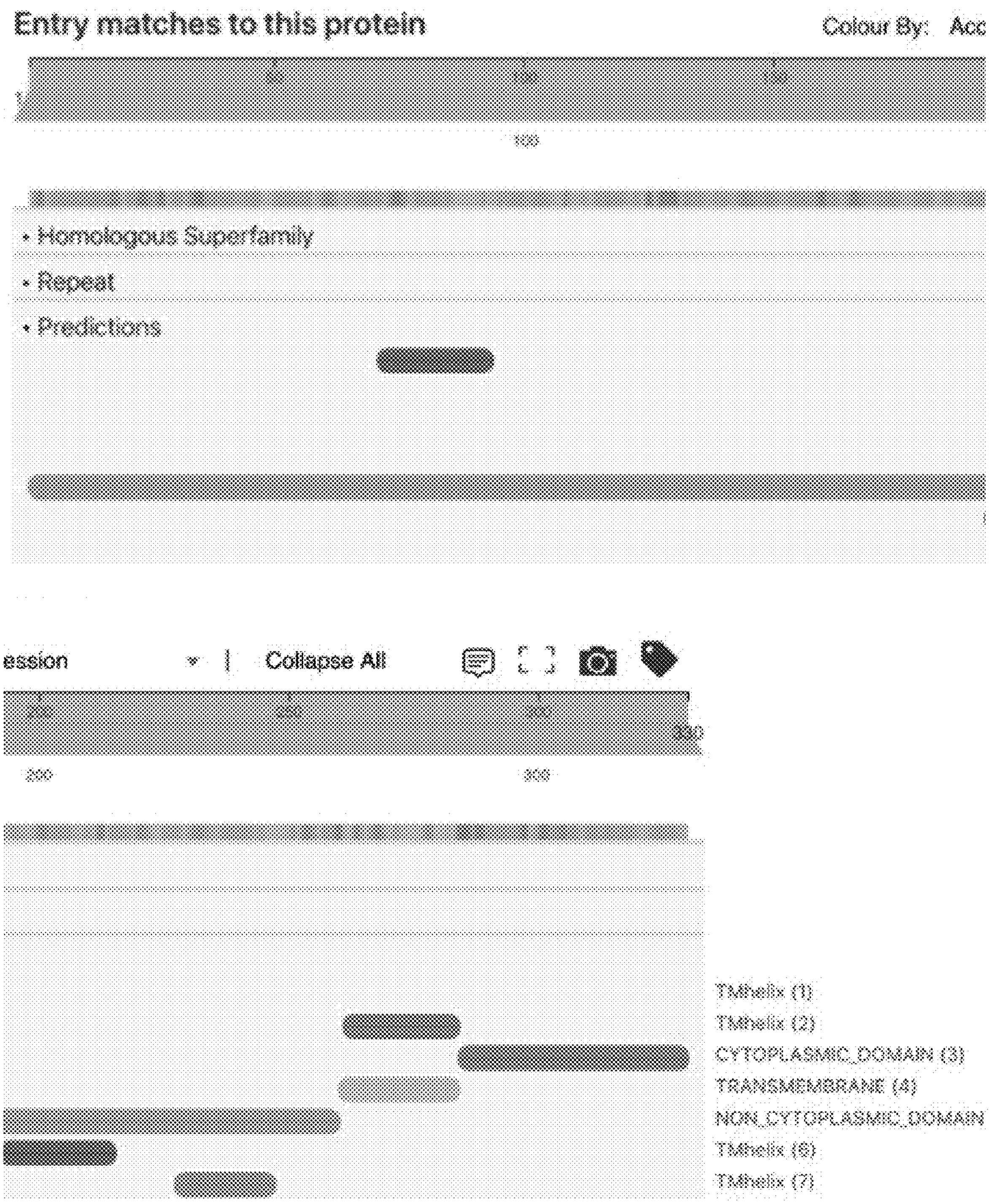
Fig. 3 (ctd)

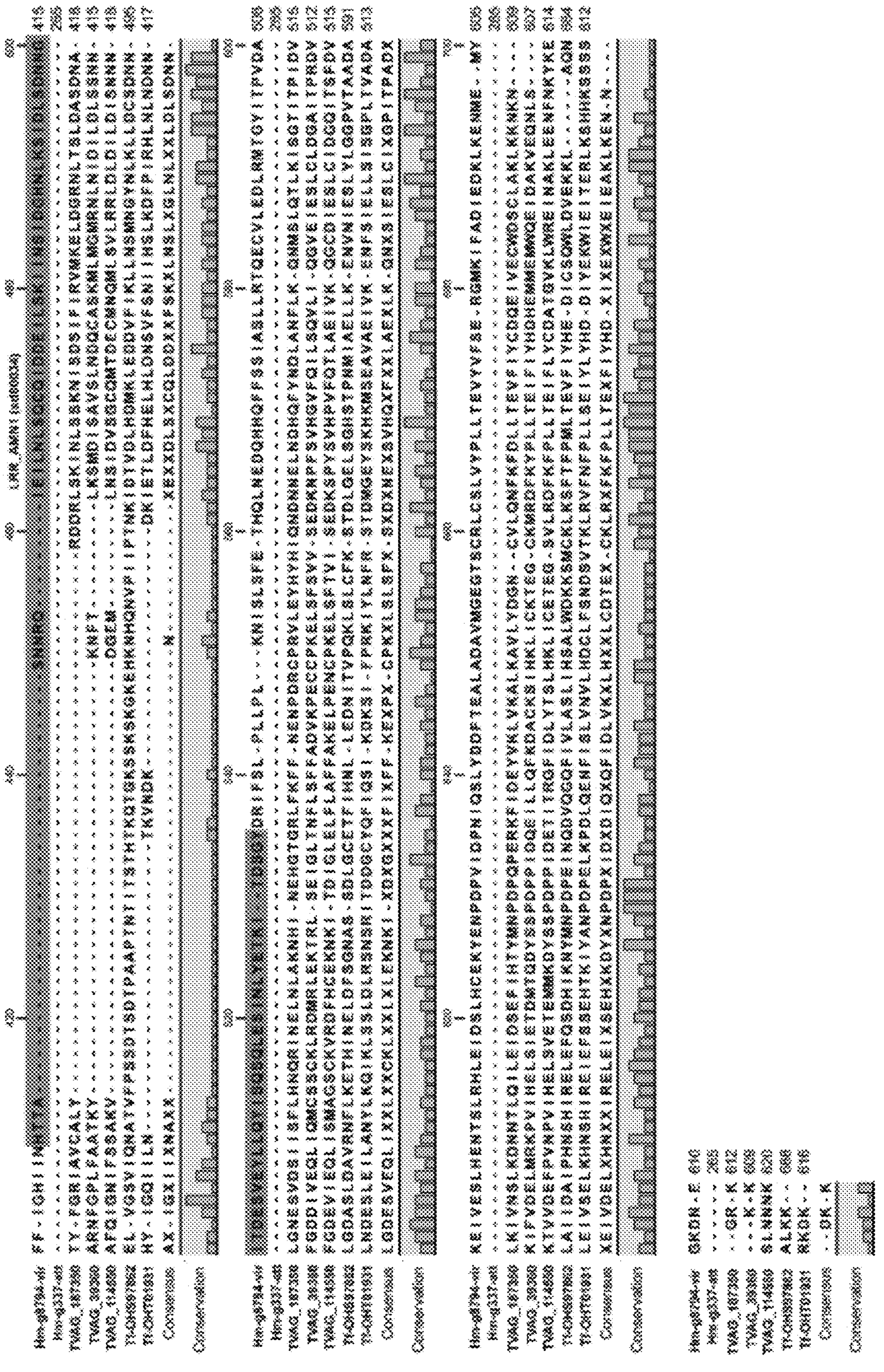
Fig. 4 (ctd)

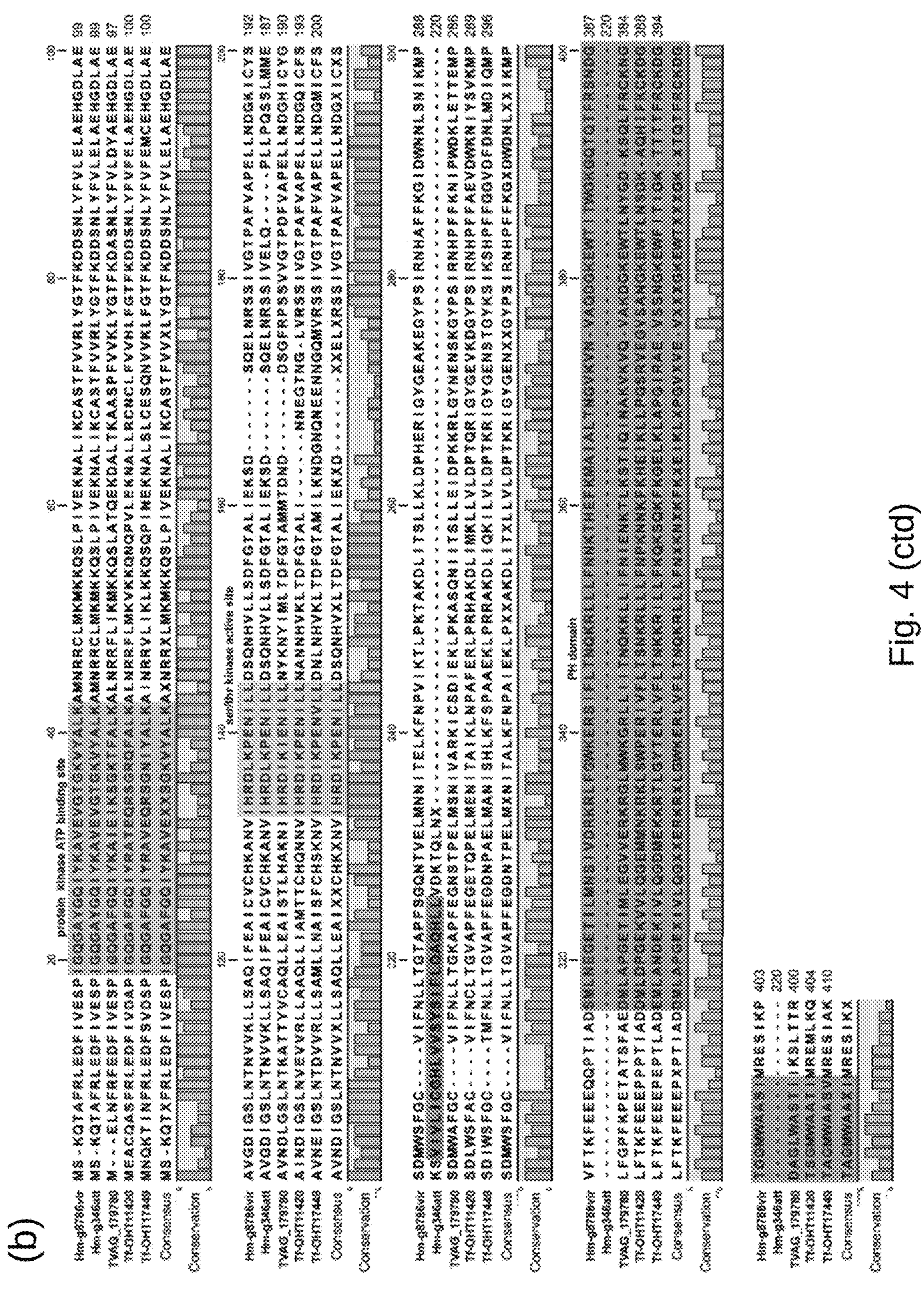
Fig. 4 (ctd)

ATTENUATED *HISTOMONAS MELEAGRIDIS* STRAIN AND VACCINE

CROSS-REFERENCE TO RELATED APPLICATIONS

This Application claims the benefit of foreign priority to EP Patent Application EP 21182469.3 filed Jun. 29, 2021, the entire disclosure of which is herein incorporated by reference.

Incorporation by Reference of the Sequence Listing

The content of the ASCII text file of the sequence listing named-1AR1888.TXT 1B78174, 4939226-4727000 bytes in size, created on Sep. 16, 2022, is incorporated herein by reference in its entirety.

BACKGROUND SECTION

The field of the invention relates to attenuated *Histomonas meleagridis* (*H. meleagridis*) strains and vaccines against histomonosis based thereon.

*H. meleagridis* is a flagellated extracellular poultry parasite of the order Tritrichomonadida. It causes histomonosis (also called histomoniasis, blackhead disease or infectious typhlohepatitis), an important disease of gallinaceous birds, especially in turkeys and chickens. The disease can be very devastating in turkeys, in which the parasite causes serious ceacal lesions and liver necrosis that can lead up to 100% mortality (McDougald, 2005). In chickens, histomonosis is typically less severe and the infection is generally confined to the caeca (Hess et al., 2015). Histomonosis and the parasite are known for more than 100 years, which in the second half of the 20th century led to the introduction of effective prophylactic and chemotherapeutic drugs with the almost disappearance of the disease (Liebhart et al., 2017). The situation drastically changed at the beginning of the present century, when these active compounds were banned as a result of amendments in drug legislation in the European Union and the USA and histomonosis reappeared with most severe consequences in turkeys (Clark & Kimminau, 2017). In addition, histomonosis became more prevalent in chickens aided by the tendency to increase free-range farming, enabling bird's easy access to the parasite.

In an attempt to prevent mortality, veterinarians can only rely on the implementation of proper flock management and the very early administration of the aminoglycoside antibiotic paramomycin, often without success. Accordingly, safe and effective vaccines against histomonosis are needed.

WO 2014/006018 A1 discloses a vaccine formulation consisting of a *Histomonas* component consisting of an attenuated culture of *H. meleagridis*, a bacterial component consisting of one or more single bacterial strains, and pharmaceutically acceptable non-biological formulation compounds.

Hess et al., 2008, discloses an attenuated culture of *H. meleagridis* which is used for the formulation of a live vaccine. EP 1 721 965 A1 also discloses such an attenuated culture.

However, producing an attenuated culture of *H. meleagridis*, especially when starting from a field isolate, is a time-consuming and laborious process when based on conventional methods such as prolonged passaging of the *H. meleagridis* cells in vitro without any guided selection for genomic traits. It is therefore an object of the present invention to provide improved methods of attenuating *H. meleagridis* as well as attenuated *H. meleagridis* strains and vaccines based thereon.

SUMMARY

The present invention provides an *H. meleagridis* strain having at least one attenuating feature selected from the group consisting of:

(a) an inactivation of a gene, wherein the gene has the sequence identified by SEQ ID NO: 1 or a sequence with at least 90%, preferably at least 93%, more preferably at least 95%, even more preferably at least 97.5%, yet even more preferably at least 98%, especially at least 99% sequence identity thereto (i.e. to the entire sequence identified by SEQ ID NO: 1), (b) an inactivation of a gene, wherein the gene has the sequence identified by SEQ ID NO: 2 or a sequence with at least 90%, preferably at least 93%, more preferably at least 95%, even more preferably at least 97.5%, yet even more preferably at least 98%, especially at least 99% sequence identity thereto (i.e. to the entire sequence identified by SEQ ID NO: 2), (c) a truncating mutation in the coding sequence of a gene, wherein the gene has the unmutated coding sequence identified by SEQ ID NO: 3 or an unmutated coding sequence with at least 95%, preferably at least 96%, more preferably at least 97%, even more preferably at least 98%, yet even more preferably at least 99%, especially at least 99.5% or even at least 99.9% sequence identity thereto (i.e. to the entire sequence identified by SEQ ID NO: 3), and (d) a truncating mutation in the coding sequence of a gene, wherein the gene has the unmutated coding sequence identified by SEQ ID NO: 4 or an unmutated coding sequence with at least 95%, preferably at least 96%, more preferably at least 97%, even more preferably at least 98%, yet even more preferably at least 99%, especially at least 99.5% or even at least 99.9% sequence identity thereto (i.e. to the entire sequence identified by SEQ ID NO: 4).

The present invention further provides an *H. meleagridis* strain having at least one attenuating feature verifiable by:

(a) a genomic PCR of the strain with forward primer AGGATGTTTCAATTTCCTCGC (SEQ ID NO: 7) and reverse primer CGGTTGTCCATTTTTCAAACAG ((SEQ ID NO: 8) not yielding a product, (b) a genomic PCR of the strain with forward primer GCGGGAAAACAAACGAAAC (SEQ ID NO: 9) and reverse primer ATAGCCATTGGTCCTGGTC (SEQ ID NO: 10) yielding a product with a size between 850 bp to 950 bp (e.g. 894 bp) comprising the sequence identified by SEQ ID NO: 15 or a sequence with at least 90%, preferably at least 93%, more preferably at least 95%, even more preferably at least 97.5%, yet even more preferably at least 98%, especially at least 99% sequence identity thereto (i.e. to the entire sequence identified by SEQ ID NO: 15), (c) a genomic PCR of the strain with forward primer TTGATTATGGGGCAACAGAAG (SEQ ID NO: 11) and reverse primer TTGGCGAAGTCTTTCAAGAG (SEQ ID NO: 12) yielding a product with a size between 450 bp to 550 bp (e.g. 488 bp) comprising the sequence identified by SEQ ID NO: 16, or (d) a genomic PCR of the strain with forward primer AAATGTTATCCATCGTGACCTC (SEQ ID NO: 13) and reverse primer GATAGCCTTCTTTGGCTTCC (SEQ ID NO: 14) yielding a product with a size between 350 bp to 450 bp (e.g. 409 bp) comprising the sequence identified by SEQ ID NO: 17.

In a further aspect, the present invention provides a method of attenuating *H. meleagridis*, comprising the steps of obtaining *H. meleagridis* cells; and introducing at least one attenuating feature selected from the group consisting of:

(a) an inactivation of a gene, wherein the gene has the sequence identified by SEQ ID NO: 1 or a sequence with at least 90%, preferably at least 93%, more preferably at least 95%, even more preferably at least 97.5%, yet even more preferably at least 98%, especially at least 99% sequence identity thereto (i.e. to the entire sequence identified by SEQ ID NO: 1), (b) an inactivation of a gene, wherein the gene has the sequence identified by SEQ ID NO: 2 or a sequence with at least 90%, preferably at least 93%, more preferably at least 95%, even more preferably at least 97.5%, yet even more preferably at least 98%, especially at least 99% sequence identity thereto (i.e. to the entire sequence identified by SEQ ID NO: 2), (c) a truncating mutation in the coding sequence of a gene, wherein the gene has the unmutated coding sequence identified by SEQ ID NO: 3 or an unmutated coding sequence with at least 95%, preferably at least 96%, more preferably at least 97%, even more preferably at least 98%, yet even more preferably at least 99%, especially at least 99.5% or even at least 99.9% sequence identity thereto (i.e. to the entire sequence identified by SEQ ID NO: 3), and (d) a truncating mutation in the coding sequence of a gene, wherein the gene has the unmutated coding sequence identified by SEQ ID NO: 4 or an unmutated coding sequence with at least 95%, preferably at least 96%, more preferably at least 97%, even more preferably at least 98%, yet even more preferably at least 99%, especially at least 99.5% or even at least 99.9% sequence identity thereto (i.e. to the entire sequence identified by SEQ ID NO: 4), into at least one of the *H. meleagridis* cells. Also provided is a cell obtainable by such method.

In another aspect, the present invention provides a vaccine comprising cells of the strain as defined herein or cells as defined herein, wherein the cells are live or inactivated, and at least one pharmaceutically acceptable excipient. This vaccine is preferably for use in prevention of histomonosis. It is preferably formulated as a gel or as a semi-solid matrix.

In yet another aspect, the present invention provides a method of vaccinating a bird against histomonosis, comprising the steps of obtaining the vaccine as defined herein and administering the vaccine to the bird.

In the course of the present invention, the genomes of a virulent *H. meleagridis* strain as well as of an attenuated *H. meleagridis* strain were sequenced to obtain the first whole genome sequences of *H. meleagridis*. Four genes were identified whose inactivation or disruption by mutation was involved in attenuation. Based on this, the strain of the present invention can be obtained e.g. by guided selection for mutations acquired during passaging or acquired by mutagenesis or, more directly, genome editing such as by CRISPR-Cas. Further, the present invention simplifies and accelerates attenuation of *H. meleagridis*, in particular also of new genotypes, thereby enabling unimpeded production of vaccines against this commercially important disease in poultry.

DETAILED DESCRIPTION

Figure 1:
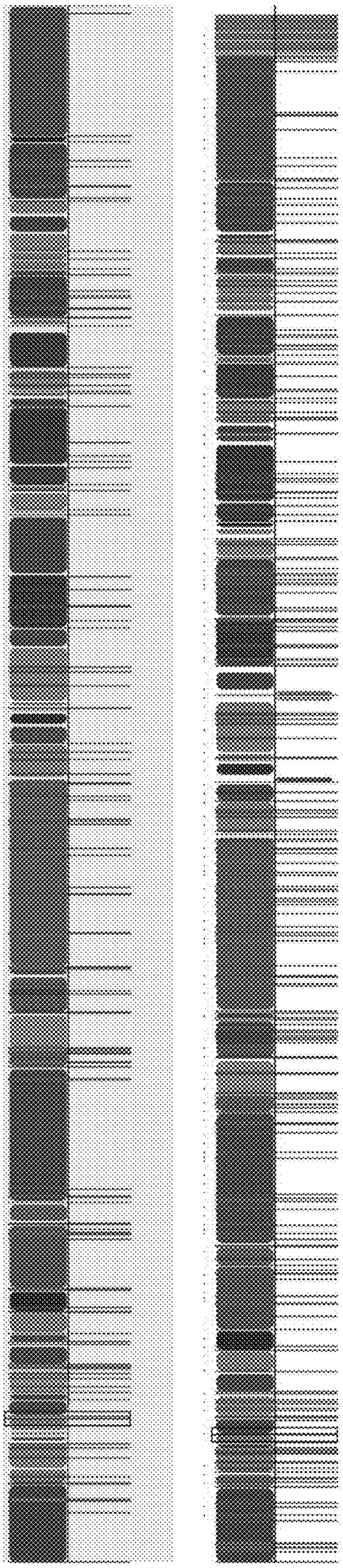
FIG. 1 Alignment of two *H. meleagridis* genomes by MAUVE (Darling et al, 2004).

The detailed description given below relates to all of the above aspects of the invention unless explicitly excluded.

The majority of early molecular studies focused on the phylogenetic positioning of *H. meleagridis*, with just a handful of research papers reporting genetic information on few protein coding genes (Bilic & Hess, 2020). Recently, omics-based approaches revealed a transcriptome, as well as the results of proteome and exoproteome analyses (Mazumdar et al, 2017; Monoyios et al, 2017; Monoyios et al, 2018; Mazumdar et al, 2019). However, the complete genome of *H. meleagridis* is not available in the prior art.

In vitro, the parasite *H. meleagridis* can typically be propagated only in the presence of bacteria (Hess et al., 2015). *H. meleagridis* is usually propagated through an in vitro xenic culture, together with turkey or chicken caecal flora. The culture may be set up by inoculating an intestinal content of a bird suffering from histomonosis into a suitable cell culture medium.

In order to standardize this procedure and to obtain a more defined culture, a clonal or mono-eukaryotic culture may be established by transferring a single *H. meleagridis* cell to fresh medium via micromanipulation (Hess et al., 2006). Further improvement of such culture can be achieved by the replacement of ill-defined caecal bacterial flora by a single bacterial strain, without compromising the virulence of the parasite (Ganas et al., 2012).

In the course of the present invention the genomes of two *H. meleagridis* strains, a monoxenic clonal virulent and an attenuated strain were sequenced. Both genomes were analysed in respect to their differing virulent phenotypes. Mutations in genes that were inactivated or modified in the course of attenuation were found. Details are disclosed in Example 1.

For stronger attenuation (and, in some cases, better growth in vitro) it is preferred when the *H. meleagridis* strain has at least two, preferably at least three, especially all of the attenuating features disclosed herein.

For similar reasons, according to a preferred embodiment, the attenuating feature(s) of the strain is/are homozygous (e.g. with respect to attenuating feature (a), (b), (c) and/or (d)).

Vaccine safety is a particular concern in live vaccines. Therefore, it is desirable when the attenuating features are stable, such that the probability for reversion to a virulent form is reduced. Accordingly, in a further preferred embodiment, the inactivation of the gene is a deletion of the gene, preferably a full deletion of the gene (e.g. with respect to attenuating feature (a) or (b)).

According to a further preferred embodiment, the truncating mutation (attenuating feature (c) and/or (d)) is a frameshift mutation or a point mutation leading to a premature stop codon. It is particularly preferred when the truncating mutation of attenuating feature (c) has the coding sequence identified by SEQ ID NO: 5 or a coding sequence with at least 95%, preferably at least 96%, more preferably at least 97%, even more preferably at least 98%, yet even more preferably at least 99%, especially at least 99.5% or even at least 99.9% sequence identity thereto (i.e. to the entire sequence identified by SEQ ID NO: 5). In addition, or alternatively thereto, it is particularly preferred when the truncating mutation of attenuating feature (d) has the coding sequence identified by SEQ ID NO: 6 or a coding sequence with at least 95%, preferably at least 96%, more preferably at least 97%, even more preferably at least 98%, yet even more preferably at least 99%, especially at least 99.5% or even at least 99.9% sequence identity thereto (i.e. to the entire sequence identified by SEQ ID NO: 6).

In a further preferred embodiment, the strain has attenuating feature (a), wherein a genomic PCR of the strain with forward primer AGGATGTTTCAATTTCCTCGC (SEQ ID NO: 7) and reverse primer CGGTTGTCCATTTTT-CAAACAG (SEQ ID NO: 8) does not yield a product. In yet another preferred embodiment, the strain has attenuating feature (b), wherein a genomic PCR of the strain with forward primer GCGGGAAAACAAACGAAAC (SEQ ID NO: 9) and reverse primer ATAGCCATTGGTCCTGGTC (SEQ ID NO: 10) yields a product with a size between 850 bp to 950 bp (e.g. 894 bp) comprising the sequence identified by SEQ ID NO: 15 or a sequence with at least 90%, preferably at least 93%, more preferably at least 95%, even more preferably at least 97.5%, yet even more preferably at least 98%, especially at least 99% sequence identity thereto (i.e. to the entire sequence identified by SEQ ID NO: 15).

In another preferred embodiment, the strain has attenuating feature (c), wherein a genomic PCR of the strain with forward primer TTGATTATGGGGCAACAGAAG (SEQ ID NO: 11) and reverse primer TTGGCGAAGTCTTT-CAAGAG (SEQ ID NO: 12) yields a product with a size between 450 bp to 550 bp (e.g. 488 bp) comprising the sequence identified by SEQ ID NO: 16.

According to another preferred embodiment, the strain has attenuating feature (d), wherein a genomic PCR of the strain with forward primer AAATGTTATC-CATCGTGACCTC (SEQ ID NO: 13) and reverse primer GATAGCCTTCTTTGGCTTCC (SEQ ID NO: 14) yields a product with a size between 350 bp to 450 bp (e.g. 409 bp) comprising the sequence identified by SEQ ID NO: 17.

In the context of the present invention, for introducing at least one attenuating feature as disclosed herein into *H. meleagridis* cells, all methods known in the art may be used. For instance, based on the gene sequences and coding sequences disclosed herein (in particular SEQ ID NOs: 1-4), targeted gene modification or knock out may be performed, in particular by CRISPR-Cas9. CRISPR-Cas9 methods have already been established in trichomonads, see e.g. Janssen et al., 2018, and Molgora et al., 2021; especially these methods may be used for the present invention. Alternatives to CRISPR-Cas9 are also available, such as gene knockout or gene replacement via selection markers, which has been established in trichomonads for a long time (see e.g. Land et al, 2003 and Bras et al, 2013. The attenuating features may also be introduced with less targeted approaches (e.g. if vaccination with genetically modified organisms is not allowed under certain regulatory regimes) long known in the art, such as by random mutagenesis followed by screening for appropriate mutants or by longer periods of in vitro cultivation followed by screening for appropriate mutants (in particular for mutants having an inactivation of the gene with the sequence identified by SEQ ID NO: 1, as this inactivation turned out to facilitate in vitro growth, thereby conferring a selective advantage).

For the present invention, the attenuating features disclosed herein can be introduced into virtually any isolate of *H. meleagridis*. Since also homogeneity of the obtained culture is usually preferred, it is a preferred embodiment of the present invention to start with a clonal culture of *H. meleagridis*, preferably a clonal culture established by micro-manipulation of a *H. meleagridis* culture. Such clonal cultures have been disclosed e.g. in EP 1 721 965 A and contain only *H. meleagridis* derived from a single cell. Such cultures are therefore homogeneous with respect to the parasite component of the culture and specifically preferred for making the strains and vaccines against *H. meleagridis* infections.

Typically, the strain or vaccine also comprises a bacterial component (which supports growth). According to a further preference, the strain is a single bacterial strain culture (as disclosed in WO 2014/006018 A1), for instance a single bacterial strain culture consisting of *H. meleagridis* and *E. coli*.

The vaccine according to the present invention is specifically for the prevention of histomonosis in birds, preferably in poultry, especially in turkey and chicken, and in game birds, especially pheasant, partridge, guinea fowl and quail.

The pharmaceutically acceptable excipient in the vaccine according to the present invention can be any compound usually contained in a vaccine, especially in a poultry vaccine. The pharmaceutically acceptable excipient can therefore be a buffer, an adjuvant, especially aluminium hydroxide, a preservative, a filler, a stabiliser, a nutrient, and usually consists of a combination of two or more of such compounds.

The vaccine can be formulated in any form suitable for a vaccine, e.g. as a tablet, especially a coated tablet, a capsule, a water-in-oil emulsion, a food product, a spray formulation, a liquid formulation, especially an additive to drinking water, an injectable formulation, especially already packaged in a syringe, as gel, as gel pad or combinations thereof. The formulation as a gel has turned out to be particularly effective for vaccinating flocks.

The vaccine according to the present invention usually comprises at least one pharmaceutically acceptable carrier or diluent such as water, saline, culture fluid, stabilisers, carbohydrates, proteins, protein containing agents such as bovine serum or skimmed milk and buffers or any combination thereof as pharmaceutically acceptable non-biological formulation compound. The stabiliser may be SPGA. SPGA contains 0.218 M sucrose (74.62 g), 0.00376 M KH2PO4 (0.52 g), K2HPO4 0.0071 M (1.25 g), potassium glutamate 0.0049 M (0.912 g) and 1% serum albumin (10 g). Various modifications of the foregoing amounts of ingredients of SPGA are known to those skilled in the art and sodium glutamate is frequently substituted for potassium glutamate, but the modified compositions are still designated as SPGA. For example, an SPGA stabilizer may contain monosodium glutamate rather than monopotassium glutamate; another SPGA stabilizer contains per liter of sterile distilled water, 74.62 g sucrose, 0.45 g KH2PO4, 1.35 g K2HPO4, 0.956 g monosodium L-glutamate, and 40 ml of a 25% solution of albuminosol (human albumin). In general, an SPGA stabilizer contains from about 2 to about 10% of sugar, e.g. sucrose; from about 0.05 to about 0.3% of a mono- or dibasic alkali metal phosphate salt or mixture thereof, e.g. KH2PO4, K2HPO4, NaH2PO4, or Na2HPO4, from about 0.05 to about 0.2% of a glutamic acid alkali metal salt, e.g. sodium or potassium glutamate; and from about 0.5% to about 2% serum albumin, e.g. bovine serum albumin or human albumin. Various substitutions of ingredients in the formulation of SPGA stabilizer can be made. For example, a starch hydrolysate, e.g. glucose or dextran may be substituted wholly or partly for sucrose and casein or PVP may be substituted wholly or partly for albumin. The carbohydrates include, for example, sorbitol, mannitol, starch, sucrose, glucose, dextran or combinations thereof. Additionally, proteins such as albumin or casein or protein containing agents such as bovine serum or skimmed milk may be useful as pharmaceutically acceptable carrier or diluents. Buffers for use as pharmaceutically acceptable carriers or diluents include maleate, phosphate, CABS, piperidine, glycine, citrate, malate, formate, succinate, acetate, propionate, piperazine, pyridine, cacodylate, succinate, MES, histidine, bis-tris, phosphate, ethanolamine, ADA, carbonate, ACES, PIPES, imidazole, BIS-TRIS propane, BES, MOPS, HEPES, TES, MOPSO, MOBS, DIPSO, TAPSO, TEA, pyrophosphate, HEPPSO, POPSO, tricine, hydrazine, glycylglycine, TRIS, EPPS, bicine, HEPBS, TAPS, AMPD, TABS, AMPSO, taurine, borate, CHES, glycine, ammonium hydroxide, CAPSO, carbonate, methylamine, piperazine, CAPS, or any combination thereof. The vaccine formulation may be lyophilized or freeze-dried. In some embodiments the vaccine according to the present invention may further comprise at least one adjuvant (in particular if the cells are inactivated). Examples of adjuvants include Freund's complete adjuvant or Freund's incomplete adjuvant, vitamin E, non-ionic block polymers, muramyldipeptides, saponins, mineral oil, vegetable oil, carbopol aluminium hydroxide, aluminium phosphate, aluminium oxide, oil-emulsions (e.g. of Bayol F® or Marcol 52®), saponins or vitamin-E solubilisate or any combination thereof. In some embodiments the vaccine may comprise adjuvants particularly useful for mucosal application for example *E. coli* heat-labile toxin or Cholera toxin. The vaccine formulation according to the present invention may be administered opthalmically (eye drop), in ovo, intradermally, intraperitoneally, intravenously, subcutaneously, orally, by spray vaccination, via the cloaca or intramuscularly. Eye drop, in ovo and spray administration are preferred when the subject is poultry. Spray administration is particularly preferred to administer the vaccine formulation to large numbers of subjects. It is specifically preferred to provide the vaccine according to the present invention in capsuled or coated form. This allows suitable preservation of the bacterium/protozoa mixture.

The vaccine according to the present invention preferably contains $1\times10^2$ to $1\times10^6$, preferably $1\times10^3$ to $5\times10^5$, especially $5\times10^3$ to $1\times10^5$ *H. meleagridis* cells per dose and/or $1\times10^5$ to $1\times10^{11}$, preferably $1\times10^7$ to $5\times10^{10}$, especially $5\times10^7$ to $1\times10^{10}$ bacterial cells (such as *E. coli*) per dose.

According to a preferred embodiment, the vaccine according to the present invention is formulated as a dose form, i.e. it is already formulated to be administered without further partition/formulation/separation steps.

The term "preventing" or "prevention" as used herein means to stop a disease state or condition from occurring in a bird completely or almost completely or at least to a (preferably significant) extent, especially when the bird is predisposed to such a risk of contracting a disease state or condition.

"Percent (%) sequence identity" with respect to a reference nucleotide sequence is defined as the percentage of nucleotides in a candidate sequence that are identical with the nucleotides in the reference sequence, after aligning the sequences and introducing gaps, if necessary, to achieve the maximum percent sequence identity, and not considering any conservative substitutions as part of the sequence identity. Gaps cause a lack of identity. Alignment for purposes of determining percent nucleotide sequence identity can be achieved in various ways that are within the skill in the art, for instance, using publicly available computer software such as BLAST, BLAST-2, ALIGN, ALIGN-2, Megalign (DNASTAR) or the "needle" pairwise sequence alignment application of the EMBOSS software package. Those skilled in the art can determine appropriate parameters for aligning sequences, including any algorithms needed to achieve maximal alignment over the full length of the sequences being compared. For purposes herein, however, % nucleotide sequence identity values are calculated using the sequence alignment of the computer programme "needle" of the EMBOSS software package (publicly available from European Molecular Biology Laboratory; Rice et al., EMBOSS: the European Molecular Biology Open Software Suite, Trends Genet. 2000 June; 16(6):276-7, PMID: 10827456).

The needle programme can be accessed under a web site or downloaded for local installation as part of the EMBOSS package. It runs on many widely-used UNIX operating systems, such as Linux.

To align two nucleotide sequences, the needle programme is preferably run with the following parameters:

Commandline: needle -auto -stdout -asequence SEQUENCE_FILE_A -bsequence SEQUENCE_FILE_B -datafile EDNAFULL -gapopen 10.0-gapextend 0.5-endopen 10.0-endextend 0.5-aformat3 pair -snucleotide1-snucleotide2 (Align_format: pair Report_file: stdout)

The % nucleotide sequence identity of a given nucleotide sequence A to, with, or against a given nucleotide sequence B (which can alternatively be phrased as a given nucleotide sequence A that has or comprises a certain % nucleotide sequence identity to, with, or against a given nucleotide sequence B) is calculated as follows:

100 times the fraction $X/Y$ where X is the number of nucleotides scored as identical matches by the sequence alignment program needle in that program's alignment of A and B, and where Y is the total number of nucleotides in B. It will be appreciated that where the length of nucleotide sequence A is not equal to the length of nucleotide sequence B, the % nucleotide sequence identity of A to B will not equal the % nucleotide sequence identity of B to A. In cases where "a sequence of A is at least N % identical to the entire sequence of B", Y is the entire length of B. Unless specifically stated otherwise, all % nucleotide sequence identity values used herein are obtained as described in the immediately preceding paragraph using the needle computer program.

"Sequence similarity", "sequence identity", "sharing a sequence" and similar terms shall also apply to the reverse complement of a sequence, i.e. the expression "sequence A is 80% identical to sequence B" shall also be true if "sequence A is 80% identical to the reverse complement (or antisense sequence) of sequence B".

The present invention is further illustrated by the following figures and examples, without being restricted thereto.

FIG. 1 Alignment of two *H. meleagridis* genomes by MAUVE (Darling et al, 2004) displaying the ortholog blocks between the virulent strain (top track) and the attenuated strain (bottom track). The red vertical lines represent the contig borders.

Figure 2:
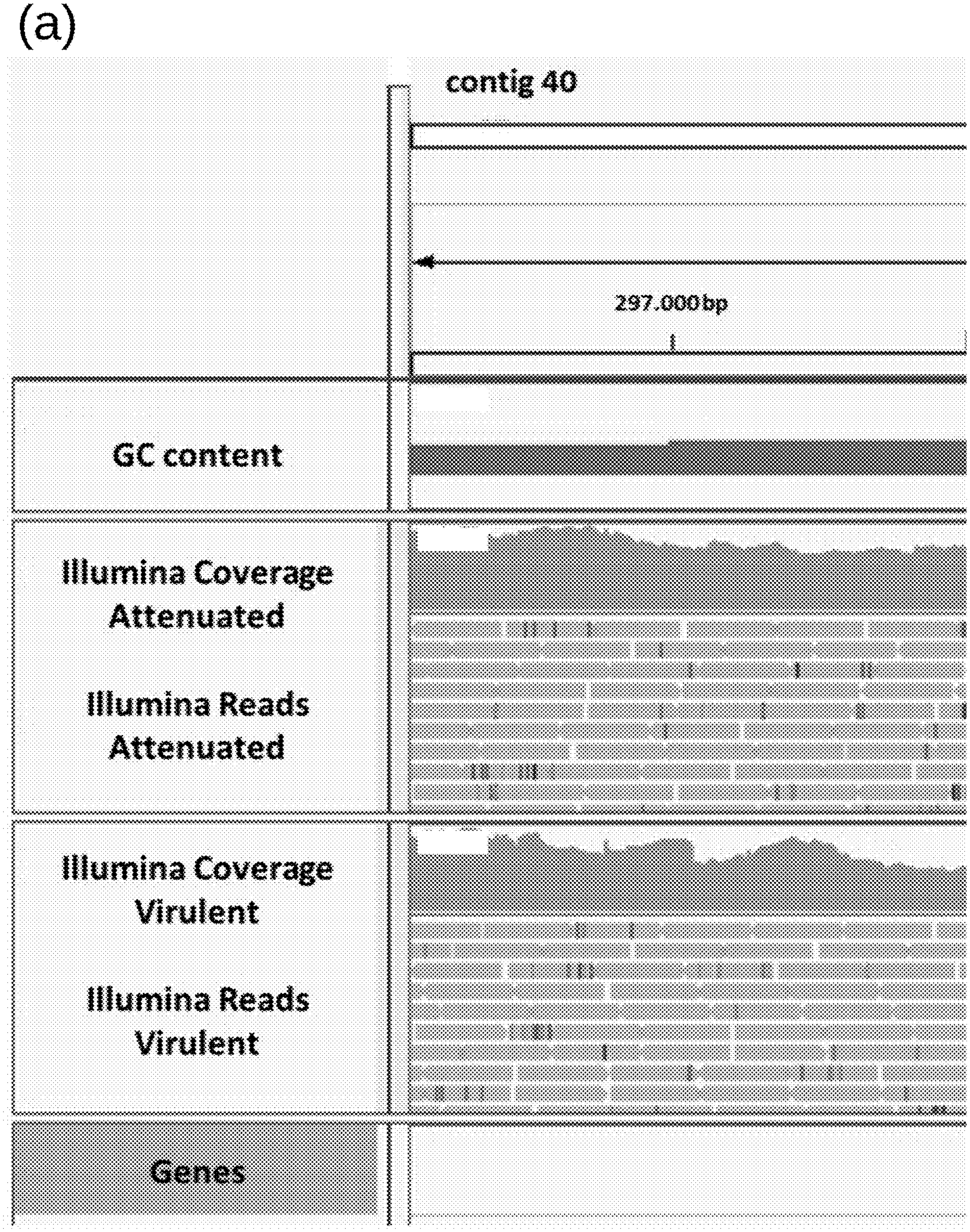
FIG. 2 Characterization of the deletion in g6116$_{vir}$: (a) Read coverage from Illumina data of both strains; (b) Domain prediction from InterProScan.

FIG. 2 Characterization of the deletion in g6116$_{vir}$: (a) Read coverage from Illumina data of both strains; (b) Domain prediction from InterProScan.

Figure 3:
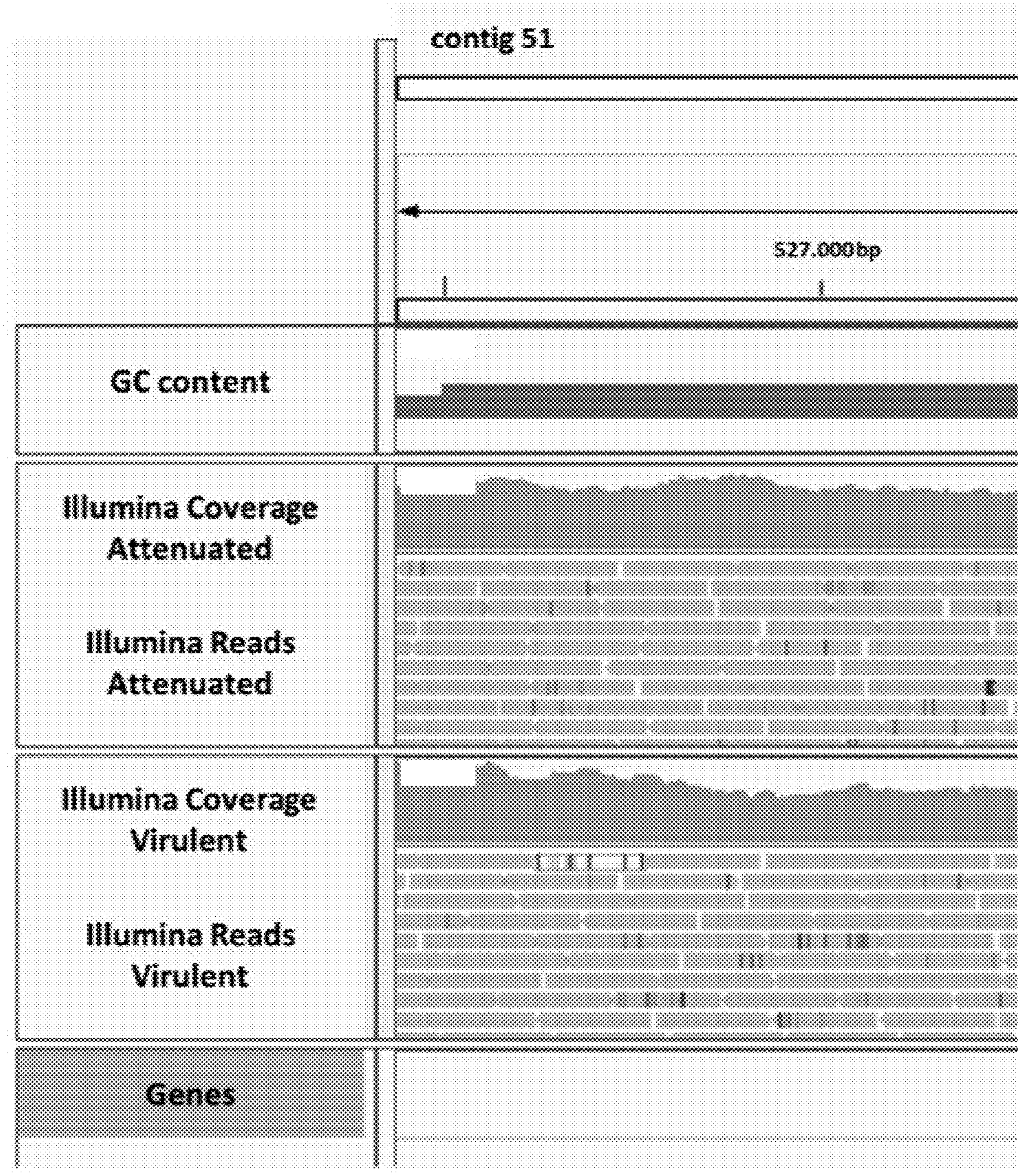
FIG. 3 Characterization of the deletion in g7085$_{vir}$: (a) Read coverage from Illumina data of both strains for the g7085$_{vir}$; (b) Pfam motif prediction showing the location of the motifs, note the presence of the BspA type motifs at the N terminus; (c) Domain prediction from InterProScan.

FIG. 3 Characterization of the deletion in g7085$_{vir}$: (a) Read coverage from Illumina data of both strains for the g7085$_{vir}$; (b) Pfam motif prediction showing the location of the motifs, note the presence of the BspA type motifs at the N terminus; (c) Domain prediction from InterProScan.

Figure 4:
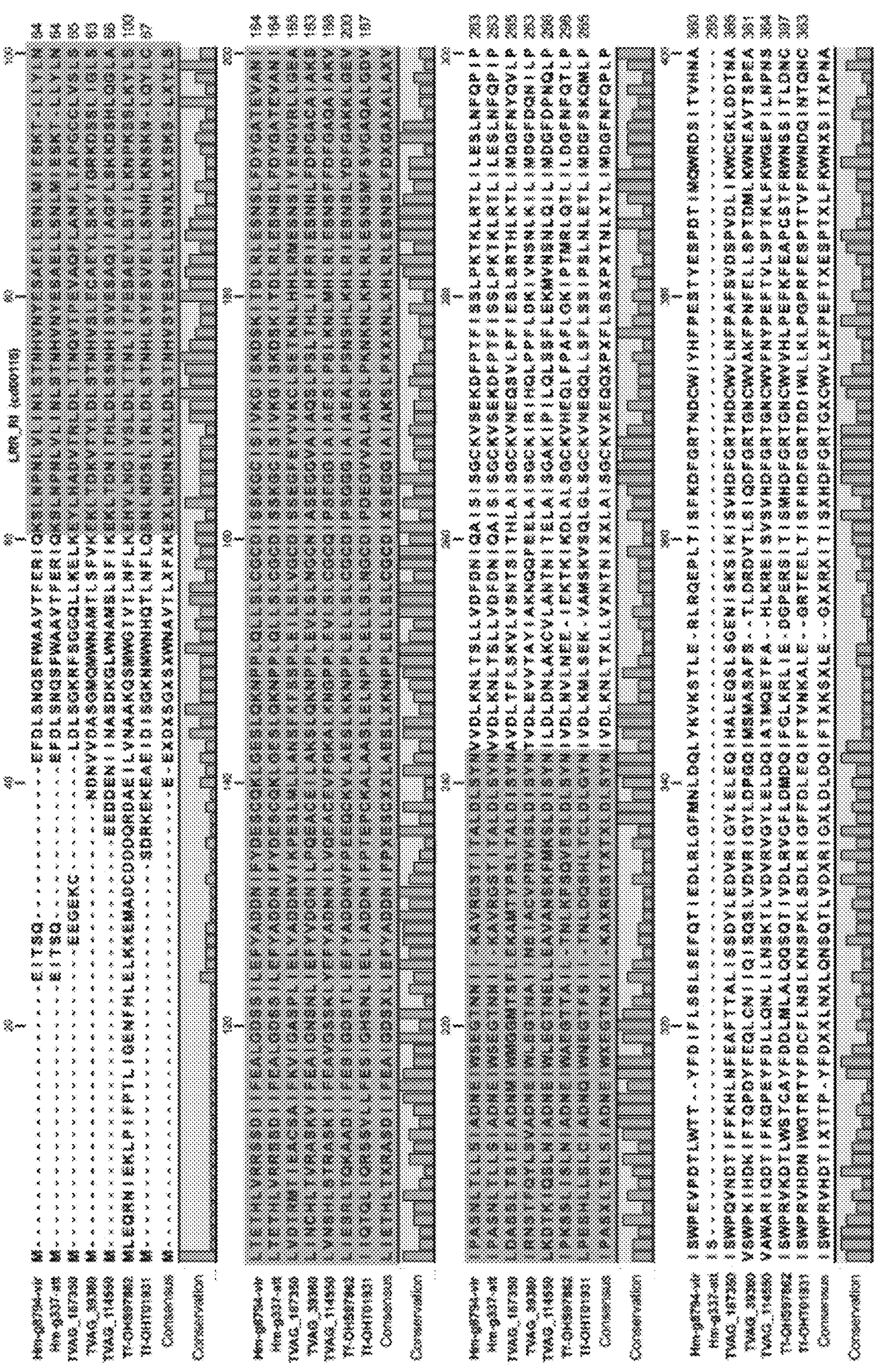
FIG. 4 Multiple amino acid alignment between the two *H. meleagridis* strains and the orthologs in *T. vaginalis* and *T. foetus* for genes displaying the truncation of the protein sequence in the attenuated strain. (a) g8794$_{vir}$/g337$_{att}$ with SNP and (b) g8786$_{vir}$/g346$_{att}$ with indel. Major protein domains are labeled. In the (a) orange box shows Leucine-rich repeats (LRRs), ribonuclease inhibitor (RI)-like subfamily conserved domain (LRR_RI (cd116)) and the grey box leucine-rich repeats, antagonist of mitotic exit network protein 1-like subfamily structural motif (LRR_AMN1 (sd00034)). In the (b) the green box designates protein kinase ATP binding site, orange box serine/threonine kinase active site, the purple a pleckstrin homology domain (PH) and the grey box a transmembrane domain in g346$_{att}$ formed due to a frameshift.

FIG. 4 Multiple amino acid alignment between the two *H. meleagridis* strains and the orthologs in *T. vaginalis* and *T. foetus* for genes displaying the truncation of the protein sequence in the attenuated strain. (a) g8794$_{vir}$/g337$_{att}$ with SNP and (b) g8786$_{vir}$/g346$_{att}$ with indel. Major protein domains are labeled. In the (a) orange box shows Leucine-rich repeats (LRRs), ribonuclease inhibitor (RI)-like subfamily conserved domain (LRR_RI (cd116)) and the grey box leucine-rich repeats, antagonist of mitotic exit network protein 1-like subfamily strucrural motif (LRR_AMN1 (sd00034)). In the (b) the green box designates protein kinase ATP binding site, orange box serine/threonine kinase active site, the purple a pleckstrin homology domain (PH) and the grey box a transmembrane domain in g346$_{att}$ formed due to a frameshift.

EXAMPLES

Example 1

Identification of Virulence Factors of *H. meleagridis*

Materials & Methods

Protozoan Cultures

Next generation sequencing experiments were performed using virulent and attenuated, monoxenic mono-eukaryotic *H. meleagridis* cultures propagated in vitro, both of which were derived from the same *H. meleagridis* cell. Cultivation was performed in the presence of *E. coli* DH5α. The cultures were incubated at 41° C. in Medium 199 containing Earl's salts, (Gibcom™, Invitrogen GmbH, Austria) supplemented with 15% heat-inactivated foetal bovine serum (FBS) (Gibco™, Invitrogen GmbH, Austria) and 0.25% of sterilized rice starch (Carl Roth GmbH+Co. KG, Germany). Cells were passaged every 3 days by transferring 2 ml of the old culture into a new T25 flask (Sarstedt, Inc., Germany).

In order to remove majority of the bacteria before sequencing, *H. meleagridis* cells were purified through a series of washing steps using pre-warmed M199 media without serum (Monoyios et al, 2017). The cell pellets were immediately frozen at −80° C. until further use.

DNA Extraction

For Illumina sequencing, DNA was extracted with QIAamp DNA Mini Kit (Qiagen, Hilden, Germany). The extraction of high molecular weight DNA, used for MINion sequencing, was performed according to a previously published protocol (Nicholls et al, 2019). Briefly, $10^8$ cells were pelleted by centrifugation at 4500×g for 10 min. The cells were re-suspended in 10 ml TLB (10 mM Tris-Cl pH 8.0, 25 mM EDTA pH 8.0, 0.5% (w/v) SDS, 20 μg/ml RNase A (Qiagen, Hilden, Germany)), vortexed at full speed for 5 seconds and incubated at 37° C. for 1 hour, with gentle mix by inversion every 30 minutes. Then, complete 100 μl of Proteinase K (Qiagen, Hilden, Germany) were added to obtain a final concentration of 200 μg/ml. The solution was gently mixed by inversion and incubated at 50° C. for 2 hours, with slow end-over-end rotations every 30 minutes. After completion, the sample was centrifuged at 200×g, and the viscous supernatant containing cell lysate was distributed into two 15 ml Falcon tubes prepared with phase-lock gel. Then, 5 ml of TE-saturated phenol pH 7.5 (Sigma-Aldrich) were added to the lysates and placed on a rotator at 20 rpm for 10 minutes. The preparations were centrifuged at 3000×g for 10 minutes and the aqueous phases were poured into two new 15 ml tubes containing phase-lock gel; followed by the addition of 2.5 ml buffer saturated phenol pH 7.5 and 2.5 ml chloroform-isoamyl alcohol 24:1 mix to each tube. Phase separation was carried out as described above and both aqueous phases were combined. The DNA was precipitated by the addition of 4 ml 5M ammonium acetate and 30 ml ice-cold 96% ethanol, for 4 days at −20° C. Precipitated DNA was collected by centrifugation at 10,000×g and washed twice in 70% ethanol. After the final spin down, the sample was air dried for 15 minutes at room temperature and 200 μl EB (10 mM Tris-Cl pH8, 0.02% (v/v) Triton X-100) were added to the DNA pellet that was kept at +4° C. until completely dissolved. DNA quantity and quality were assessed using Qubit™ dsDNA BR Assay Kit (Invitrogen, Life technologies), NanoDrop 2000 (Thermo Fisher Scientific) and Agilent 4200 TapeStation System using Genomic DNA Screen tape (Agilent technologies).

Illumina Sequencing

For each *H. meleagridis* strain a paired-end Illumina library was prepared from 1.5 μg DNA using TruSeq DNA PCR-Free Library Kit (Illumina). Sequencing (150 bp PE) was carried out on Illumina HiSeq 3000/4000 platform. Resulting reads were imported into CLC Genomics Workbench 12.0 quality trimmed and adapters were removed. The processed reads were assembled into contigs using the De Novo Assembly workflow.

Libraries for Nanopore sequencing were prepared from 0.8 μg of high molecular weight *H. meleagridis* DNA using SQK-LSK109 1D ligation kit (Oxford Nanopore Technologies, Oxford, UK). Libraries were sheared by using the g-TUBE (Covaris) and centrifuged at 6,000 rpm in an Eppendorf 5424 centrifuge for 2×1 min, inverting the tube between centrifugations. DNA repair (NEBNext® FFPE DNA Repair Mix, M6630S, New England Biolabs GmbH, Frankfurt am Main, Germany) and End repair/dA-tailing (NEBNext® Ultram II End Repair/dA-Tailing Module, New England Biolabs GmbH, Frankfurt am Main, Germany) were performed by adding 27 μl nuclease-free water (NFW), 3.5 μl FFPE Repair Buffer, 2 μl FFPE DNA Repair Mix, 3.5 μl Ultra II End-prep reaction buffer and 3 μl Ultra II End-prep enzyme mix to 20 ul of the previously sheared DNA in a 0.2 ml thin-walled PCR tube. Using a thermocycler, the mixture was incubated at 20° C. for 5 minutes and 65° C. for 5 mins. The preparation was transferred to a 1.5 ml Eppendorf DNA LoBind tube and cleaned up using a 60

μl of Agencourt AMPure XP beads (Beckman Coulter Life Sciences, Vienna, Austria), incubated at room temperature with end over end mixing for 5 min, washed twice with 200 μl fresh 70% ethanol and allowed to air dry for 30 seconds. Adapter Ligation was performed by adding 60 μl DNA sample from the previous step, 25 μl Ligation Buffer (LNB), 10 μl T4 DNA Ligase (NEBNext® Quick Ligation Module) and 5 μl Adapter Mix (AMX) in a 1.5 ml Eppendorf DNA LoBind tube, incubating the preparation at room temperature for 10 min. The adaptor-ligated DNA was cleaned up by adding 40 μl of Agencourt AMPure XP beads (Beckman Coulter, Life Sciences, Vienna, Austria), incubated at room temperature with end over end mixing for 5 min. The beads were washed twice with 250 μl Long Fragment Buffer (LFB) and allowed to air dry for 30 seconds. The DNA was eluted by adding 15 μl Elution Buffer (EB) and incubated for 10 minutes at 37° C. Flow Cell Priming was carried out with the introduction of 800 μl of the priming mix into the flow cell via the priming port, with a 5-minute incubation period. The DNA Library was prepared for loading adding 37.5 μl Sequencing Buffer (SQB) and 25.5 μl Loading Beads (LB) to 12 μl of the previously generated DNA Library. Flow cells (FLO-MIN106) were run with the standard MinKNOW software. Base calling option was enabled for a run duration of ~48 h, with a Bias Voltage of −180 mV and time between mux scans of 1.5 h.

Genome Assembly and Annotation

For processing of Nanopore reads, FAST5 files were converted to FASTQ using the Guppy basecaller followed by adapters trimming with Porechop. A draft assembly was generated using Flye (parameters –g 50 m—meta) from the Nanopore reads. To scan for *E. coli* contigs and contaminations, the draft assembly was divided into 1 Kb windows and analyzed through the Taxonomic Profiling tool of CLC Genomics Workbench 12, Microbial Genomics Module (Qiagen, Hilden, Germany) against the complete bacterial genome database. Contigs matching in their entirety to bacteria were removed from the draft assembly. For assembly refining, Illumina reads were subsampled to 30 million and aligned to the draft assembly by minimap2 (Li, 2018) (default parameters) followed by three rounds of refining with racon (Vaser et al, 2017) (default parameters). The quality of the refined assembly was evaluated in the following way: a reference assembly made only from Illumina reads was constructed using the De Novo Assembly tool from CLC Genomics Workbench 12 (Qiagen, Hilden, Germany), as Illumina reads have higher base-level accuracy compared to Nanopore reads. Then, the average similarity between the refined assembly and the Illumina assembly was computed by the program dnadiff of the MUMmer package (Marcais et al, 2018). To evaluate genome completeness, a set of eukaryotic core genes was downloaded from the CEGMA web page and BLASTed to the refined assembly (E-value<$10^{-3}$) in order to estimate the percentage of eukaryotic core genes in the refined assembly. For genome annotation, the transcriptome dataset from Mazumdar et al., 2017, was used as input for training of the AUGUSTUS gene predictor using the web interface of this tool (Hoff & Stanke, 2013). After training, the local version of AUGUSTUS (Stanke et al., 2006) was run on the refined assembly of each strain (parameters—strand-both—genemodel=partial). Functional annotation of coding genes was made using the Blast2GO tool from CLC Genomics Workbench 12 (Qiagen, Germany). Annotation of repetitive sequences and transposons was performed by RepeatMasker 4.0.7 assessed in November 2019 (parameters—species "trichomonas") (Smit et al, 2013).

Identification of variants between the genomes of virulent and attenuated *H. meleagridis* strains For variants identification (single-nucleotide polymorphisms—SNPs—and indels), the assembly of the attenuated strain was aligned against the virulent strain using nucmer from the MUMmer package (Marcais et al, 2018) followed by variant calling with the show-snps tool (parameters -C -l -r). To validate the accuracy of variant calling, Illumina reads from both strains were aligned to the assembly of the virulent strain with Bowtie2 (default parameters) (Langmead & Salzberg, 2012). Then, variants with minimum coverage of 30 in both strains and minimum reference allele frequency of 80% were regarded as true homozygous SNPs (or indels) between the two strains. SNPs located in coding regions were extracted and their potential impact on protein stability was predicted using the online tool PROVEAN (Choi & Chan, 2015).

Confirmation of variants between virulent and attenuated strains

In order to validate variants that caused premature stops in the corresponding coding regions, conventional PCRs were performed. To confirm the two deletions, conventional and real-time PCRs were employed. Real-time PCRs were done in 20 μl reaction mixture on the AriaMx real time cycler (Agilent Technologies, USA) using Brilliant III Ultra-Fast qPCR Master Mix (Agilent Technologies, USA) with 30 nM ROX as reference dye, 500 nM primers and 100 nM TaqMan probe. Thermal profile of real-time reactions was as follows: 15-minute at 95° C., followed by 40 cycles of 15 seconds at 95° C. and of 30 seconds at 60° C. Fluorescence was detected and reported at each cycle during the 60° C. step. All conventional PCRs were performed in 25 μl reaction by using HotStar Taq Master Mix Kit (Qiagen, Vienna, Austria) and 0.4 μM of each primer. Thermo-cycling conditions for all conventional PCRs were: one cycle of 95° C. for 15 minutes; 40 cycles of 95° C. for 30 seconds, 51° C. or 52° C. (depending on the target region) for 30 seconds and 72° C. for 1 minute; followed by final elongation step at 72° C. for 10 minutes. Amplification products (25 μl) were electrophoresed in a 1.0% Tris acetate-EDTA-agarose gel, stained with ethidium bromide and visualized under UV light (Biorad Universal Hood II, Bio-Rad Laboratories, California, USA). Fragment sizes were determined with reference to a lkb ladder (Invitrogen, Life Technologies, Austria). Amplification products (25 μl) were electrophoresed in a 1.0% Tris acetate-EDTA-agarose gel, stained with ethidium bromide and visualized under UV light (Biorad Universal Hood II, Bio-Rad Laboratories, California, USA). Fragment sizes were determined with reference to a 1 kb ladder (Invitrogen, Life Technologies, Austria). PCR products of the expected sizes were excised from the gel and purified using the QIAquick Gel Extraction Kit (Qiagen, Vienna, Austria) according to the manufacturer's instructions. Direct fluorescence-based sequencing was performed by LGC Genomics GmbH (Berlin, Germany) using the PCR primers.

Sequences

TABLE 1 lists *H. meleagridis* sequences found in the course of the present invention:

| SEQ ID NO | description | sequence |
|---|---|---|
| 1 | g6116$_{vir}$ gene sequence | ATGGCAACAACTAATACAACAGCGGCGATTACAATGCCGACAACTGCCTCTGTTGTAACA<br>GAACTTTCTTGTGCGGGTTCCTCTGATGTTGATGGAACTTGTTCGGATGAAACTGCTGTG<br>CTTGTGACGGGCTCTGGTTCTTGTGTCTCTGTTCCTTCAGTGGCTTCTGTTGTCTCAGTA<br>ACTATAGAAGTAACTGCAGAAGAGTGTTCTTCAGTGGTGTGAACTGAAGATGAAGATTCG<br>GTTGAGGATTCGACGGATGATTCTGATGCAGGCTCACTGGATGACTCAATAGAAGATTCA<br>GATACTGATTCACTTGATGATTCTGATACTGATTCAGATGAGGACTCAGATGATGATTCT<br>GATGAAGATTCTGATACTGATTCACTTGAAGATTCACTAGATGATTCACTAGATGATTCA<br>GATGAAGATTCACTAGAGGATTCTGATGAAGATTCACTAGATGATTCACTAGATGATTCA<br>GATGAAGATTCACTAGAGGATTCTGATGAAGATTCACTAGATGATTCACTTGAGGATTCT<br>GATGAAGATTCACTAGATGATTCACTTGAGGATTCTGATGAAGATTCACTAGAGGATTCT<br>GATGAAGATTCACTAGATGATTCACTTGAGGATTCTGATGAAGATTCACTAGATGATTCA<br>CTTGAGGATTCTGATGAAGATTCACTTGAGGATTCACTAGATGATTCAGATGAAGATTCA<br>CTAGATGATTCACTTGAGGATTCTGATGAAGATTCACTTGAGGATTCTGATGAAGATTCA<br>CTTGAGGATTCTGATGAAGATTCACTAGATGATTCACTTGAGGATTCTGATGAAGATTCA<br>CTTGAGGATTCTGATGAAGATTCACTTGAGGATTCTGATGAGGACTCACTTGAGGATTCT<br>GATGAAGATTCACTTGAGGATTCTGATGAAGATTCACTTGAGGATTCTGATGAAGATTCA<br>CTAGATGATTCACTTGAGGATTCTGATGAAGATTCACTAGAGGATTCTGATGAAGATTCA<br>CTAGATGATTCACTTGAGGATTCTGATGAAGATTCACTTGAGGATTCTGATGAAGATTCA<br>CTAGATGATTCACTTGAGGATTCAGATGAAGATTCACTAGATGATTCAGATGAAGATTCA<br>CTTGAGGATTCTGATGAAGATTCACTTGAGGATTCTGATGAAGATTCACTTGAGGATTCT<br>GATGAGGACTCACTTGAGGATTCTGATGAAGATTCACTTGAGGATTCTGATGAAGATTCA<br>CTTGAGGATTCTGATGAAGATTCACTAGATGATTCACTTGAGGATTCTGATGAAGATTCA<br>CTTGAGGATTCTGATGAAGATTCACTAGATGATTCACTTGAGGATTCAGATGAAGATTCA<br>CTAGATGATTCAGATGAAGATTCACTTGAGGATTCTGATGAGGACTCACTTGAGGATTCT<br>GATGAAGATTCAGATGAAGATTCACTTGAGGATTCTGATGAAGATTCACTAGATGATTCA<br>CTTGAGGATTCTGATGAAGATTCACTAGATGATTCACTTGAGGATTCTGATGAAGATTCA<br>GATGAAGATTCACTTGAGGATTCTGATGAAGATTCACTAGATGATTCACTTGAGGATTCA<br>GATGAAGATTCACTTGAGGATTCTGATGAAGATTCACTTGAGGATTCTGATGAAGATTCA<br>CTTGAGGATTCTGATGAAGATTCACTAGATGATTCACTTGAGGATTCTGATGAAGATTCA<br>CTTGAGGATTCTGATGAAGATTCAGATGAAGATTCACTTGAGGATTCTGATGAAGATTCA<br>CTAGATGATTCACTTGAGGATTCAGATGAAGATTCACTAGATGATTCAGATGAAGATTCA<br>CTTGAGGATTCTGATGAAGATTCACTAGATGATTCACTTGAGGATTCTGATGAAGATTCA<br>CTTGAGGATTCTGATGAAGATTCACTTGAGGATTCTGATGAGGACTCACTTGAGGATTCT<br>GATGAAGATTCACTAGATGATTCACTTGAGGATTCTGATGAAGATTCACTTGAGGATTCT<br>GATGAAGATTCACTAGATGATTCACTTGAGGATTCTGATGAAGATTCACTTGAGGATTCT<br>GATGAAGATTCACTTGAGGATTCTGATGAGGACTCACTTGAGGATTCTGATGAAGATTCA<br>CTTGAGGATTCTGATGAAGATTCACTAGATGATTCACTTGAGGATTCTGATGAAGATTCA<br>CTAGATGATTCACTTGAGGATTCTGATGAAGATTCACTAGAGGATTCTGATGAAGATTCA<br>CTAGAGGATTCTGATGAAGATTCACTTGAAGATTCTGATGAGGACTCACTTGAGGATTCT<br>GATGAAGATTCACTTGAGGATGTTTCAATTTCCTCGCCGCCGCCCTGGCCGCCACCGCCT<br>TCTTCTTCGTCGCCGTCGCCGCCGCCGCCTTCTTCGCCGCCTTCGTTGCCATCAGCTAGT<br>AATTGGAGATTGAATTTTTTCATTGATTTTGTTAAGCGTTCTAGTTCTGTTTCTTGGCCA<br>AAAAGGGCTTGTTCGAGATTACTTTCTTTTTTGTTTATATTGGCTGGTCTTGCGAGTAGG<br>ATCAGGAAGAGTCCAAACATGATAGTGACAAAAAATCAAGTTTTTGAGAGCTGCTCTGAA<br>TTTTGA |
| 2 | g7085$_{vir}$ gene sequence | ATGATTAAAGTTTCCAGCGAAAATGCAAATTATTGCAATTATAACGAAGATGGGATTTTA<br>TATAACAAAAACGTCACTAAAATTATATGTTATCCATGCGGGAAAACAAACGAAACATAT<br>ACATTCCCAACAAATGCCAGTGTTATTGATATTAATGCATACTGTAATTGTATTTCATTA<br>AGGAACATTGAAATTCCATGCAATATAACGTCAGTTGGAAGCAAAGCATTTGCATCATGC<br>TGCAATCTCACATGTATTTTTTTTTTTTTTTTTACAGTCCCAACGAATACATCGAATGTA<br>CCTGATGACAACAATTTAATCAGAAGTGTCCTGACAATCGATTCATATAACGGCCAAACA<br>TTCTGCGGTATAAAAGTCAGTAAAGGAAAAGTCATTGATGAATGTCTCCCACCGACGCAA<br>TCGTTCACACGATCGAACACATACTCAAACACATTTACTCAGTCGAATACGTTCACTAAG<br>TCGAATACATTCACTAAGACGAATACATTTACTCAGTCGAATACATTATTACCTTCGAAT<br>GTAACGCTGACACTTTCGTTTACGAATTCATATTCCATCACTGAAACTGTTACAATTTCT<br>GGTACATATTCTTATTCATATGTTTTGACTTTAATTGGAGTTAGTAGTACATATGTCAGA<br>ACAGATTTAATTTATTATGAATATATTGTGACTCGTTATTCGACGTTATATAGTTTTTAT<br>TCGAATTTCTTCACAATTATCGACGTCATAAATCCTGTTGGAAATGGTATTTCTCAAAAG<br>GCTTTGATAGGTATTATCTGCGGCACAATAATTGCAGTTTTGCTGATTATGGGAATTATC<br>ATATTCCTTGTGAAGAAATCAAAGAAAAGTAACAGCGAATCAACAGCGATAAAATTCGAA<br>ACTAAAAATTCAACTGGAAGCGATATGAGATCAGATGAAGTAAATCAGGAATATAATGAA<br>CTCGTGTTGGAAGACCAGGACCAATGGCTATAA |
| 3 | g8794$_{vir}$ coding sequence (CDS) | ATGGAAATTACTTCCCAAGAATTTGATCTTTCAAACCAATCATTTTGGGCAGCAGTCACA<br>TTTGAGCGAATTCAAAAAAGCCTAAATCCGAATCTAGTTTTAATTAATCTTTCTACAAAT<br>CATGTTAATTATGAATCAGCAGAACTTTTATCAAACTTAATGATAGAGAGCAAGACTTTA<br>CTTTACTTAAATCTTACAGAAACCCATTTAGTTAGGCGCTCTTCTGATATAATTTTTGAA<br>GCTCTTGGAGATTCATCAATTCTTGAATTTTATGCAGATGATAATATTTTTTACGACGAA<br>AGTTGTCAAAAGCTTGGTGAGTCATTACAGAAAAATCCACCTCTTCAACTCTTAAGCTTG<br>TGTGGATGCGACATTTCATCAAAAGGGTGCATTTCAATTGTAAAAGGAATTTCAAAGGAT |

TABLE 1-continued lists *H. meleagridis* sequences found in the course of the present invention:

| SEQ ID NO | description | sequence |
| --- | --- | --- |
| | | TCAAAAATAACCGATTTACGGTTAGAGTCAAATTCTTTATTTGATTATGGGGCAACAGAA<br>GTTGCAAATATTATACCAGCATCAAACTTAACCTTACTCAGTATCGCTGACAATGAAATA<br>TGGAGTGAAGGGACAAATAATATCATTAAAGCTGTTCGAGGTAGTACTATCACTGCATTA<br>GATTTAAGTTATAACGTGGTTGACTTAAAAAACCTCACTAGCTTGTTGGTAGATTTTGAT<br>AACATACAAGCCATTAGTATCAGTGGATGTAAAGTTTCTGAAAAAGATTTTCCAACTTTT<br>ATTTCGTCACTTCCAAAAACAAAATTAAGAACTCTTATCTTGGAAAGCCTTAATTTCCAA<br>CCTATTCCAATCTCTTGGCCCGAAGTTCCTGATACCTTATGGACAACATATTTTGATATC<br>TTTTTATCATCTTTATCAGAATTCCAAACGATAGAAGATCTTCGACTTGGCTTTATGAAT<br>CTAGATCAACTTTATAAAGTCAAGTCAACTCTTGAAAGACTTCGCCAAGAACCTTTAACA<br>ATTAGTTTTAAAGATTTTGGTCGAACTAATGATTGTTGGATATATCATTTTCCTGAATCC<br>ACGTATGAAAGTCCAGATACCATTATGCAATGGCGCGATAGCATCACAGTGCACAACGCG<br>TTCTTCATCGGCCACATCATCAATCACACCACCGCATCAAATAACCGTCAAATTGAAATT<br>TTGAATTTGAGTCAGTGTCAAATTGACGATGAAATTTTATCCAAAATCATCAACAGCATC<br>GACGGCCATAACCTTAAGAGCATCGATTTAAGTGATAATAATGGCATTACTGATGAATCC<br>GTCGAATATCTTCTTCAATATATCTCTCAATCGCAACTTGAATCAATTAATCTTTATGAA<br>acaaaaatcacagattcaggctatgaccgcattttctctcttccacttctccctcttaag<br>AACATTTCTCTCTCATTTGAAACACATCAATTAAATGAAGATCAACATCATCAATTTTTT<br>AGTAGCATCGCATCACTCTTACGAACGCAAGAATGTGTTCTCGAGGACTTACGGATGACG<br>GGCTATATCACTCCAGTTGACGCCAAAGAAATTGTCGAATCGTTACACGAGAACACAAGT<br>TTGAGGCATTTGGAAATCGACAGTTTGCACTGCGAGAAGTACGAAAACCCCGATCCAGTG<br>ATAGATCCGAACATACAGAGCCTCTACGACGACTTCACCGAAGCGCTTGCGGATGCAGTG<br>ATGGGCGAAGGCACTTCATGCAGACTATGCTCACTCGTGTACCCGCTGCTGACTGAGGTA<br>TATGTGTTCAGCGAACGAGGAATGAAAATATTCGCTGACATTGAGGATAAGCTGAAAGAA<br>AATATGGAAATGTATGGGAAGGATAATGAGTGA |
| 4 | g8786$_{vir}$ CDS | ATGTCGAAACAGACAGCATTTCGCCTTGAAGATTTTATTGTTGAATCCCCAATAGGCCAA<br>GGCGCATACGGTCAAATTTATAAAGCTGTTGAAGTTGGAACTGGAAAAGTTTATGCATTA<br>AAAGCAATGAATAGAAGATGTCTTATGAAGATGAAAAAACAAAGCCTACCAATTGTAGAA<br>AAAAATGCACTAATTAAGTGTGCTAGTACTTTTGTTGTTCGTTTATATGGAACGTTCAAG<br>GATGATTCAAATTTGTATTTTGTACTTGAATTAGCAGAACATGGTGACCTTGCAGAAGCC<br>GTAGGGGATATTGGAAGTCTTAACACTAATGTAGTTAAACTTCTTTCTGCTCAAATTTTT<br>GAAGCAATCTGTGTATGTCATAAAGCAAATGTTATCCATCGTGACCTCAAGCCAGAAAAC<br>ATTCTCCTCGACTCGCAAAACCACGTTCTTCTCTCAGATTTTGGTACAGCCCTAATTGAA<br>AAATCTGATAGTCAAGAATTAAATCGTTCATCCATTGTTGGAACTCCAGCCTTTGTTGCC<br>CCAGAGCTCCTTAATGATGGAAAAATCTGTTATAGTTCTGATATGTGGTCATTTGGTTGT<br>GTCATATTCAATCTTCTTACAGGCACAGCACCTTTTAGTGGACAAAACACAGTTGAATTA<br>ATGAACAACATCACTGAGCTTAAGTTTAATCCAGTCATTAAAACACTTCCGAAAACCGCC<br>AAAGATCTCATCACATCCTTACTTAAGCTTGATCCACACGAGCGTATTGGATACGGGGAA<br>GCCAAAGAAGGCTATCCCTCCATTCGTAACCATGCCTTTTTCAAAGGCATTGATTGGAAT<br>AATTTGTCAAATATCAAAATGCCTGTTTTCACCAAATTCGAAGAAGAACAACAACCAACC<br>ATTGCAGATTCCATGCTAAATGAAGGGGAGACCATTCTAATGAATAGTATTGTCGACAGA<br>AAGCGATTATTTGGTTGGAAAGAGCGTTCGATATTTTTGACTAATCAAAAGAGACTTTTG<br>TTATTTAACAACAAAACGCACGAGTTTAAGATGGCAATAGCATTAACGAATGGAGTCAAA<br>GTGAATGTTGCACAAGATGGGAAAGAATGGACAATCACTTGGGGAAAAGGCCAAACGCAA<br>ACATTTAGATCAAATGATGGAACTGGCGGAATGTGGGCAGCATCAATAATGAGGGAATCA<br>ATCAAACCATAA |
| 5 | g337$_{att}$ CDS | ATGGAAATTACTTCCCAAGAATTTGATCTTTCAAACCAATCATTTTGGGCAGCAGTCACA<br>TTTGAGCGAATTCAAAAAAGCCTAAATCCGAATCTAGTTTTAATTAATCTTTCTACAAAT<br>CATGTTAATTATGAATCAGCAGAACTTTTATCAAACTTAATGATAGAGAGCAAGACTTTA<br>CTTTACTTAAATCTTACAGAAACCCATTTAGTTAGGCGCTCTTCTGATATAATTTTTGAA<br>GCTCTTGGAGATTCATCAATTCTTGAATTTTATGCAGATGATAATATTTTTTTACGACGAA<br>AGTTGTCAAAAGCTTGGTGAGTCATTACAGAAAAATCCACCTCTTCAACTCTTAAGCTTG<br>TGTGGATGCGACATTTCATCAAAAGGGTGCATTTCAATTGTAAAAGGAATTTCAAAGGAT<br>tcaaaaataaccgatttacggttagagtcaaattctttatttgattatggggcaacagaa<br>GTTGCAAATATTATACCAGCATCAAACTTAACCTTACTCAGTATCGCTGACAATGAAATA<br>TGGAGTGAAGGGACAAATAATATCATTAAAGCTGTTCGAGGTAGTACTATCACTGCATTA<br>GATTTAAGTTATAACGTGGTTGACTTAAAAAACCTCACTAGCTTGTTGGTAGATTTTGAT<br>AACATACAAGCCATTAGTATCAGTGGATGTAAAGTTTCTGAAAAAGATTTTCCAACTTTT<br>ATTTCGTCACTTCCAAAAACAAAATTAAGAACTCTTATCTTGGAAAGCCTTAATTTCCAA<br>CCTATTCCAATCTCTTGA |
| 6 | g346$_{att}$ CDS | ATGTCGAAACAGACAGCATTTCGCCTTGAAGATTTTATTGTTGAATCCCCAATAGGCCAA<br>GGCGCATACGGTCAAATTTATAAAGCTGTTGAAGTTGGAACTGGAAAAGTTTATGCATTA<br>AAAGCAATGAATAGAAGATGTCTTATGAAGATGAAAAAACAAAGCCTACCAATTGTAGAA<br>AAAAATGCACTAATTAAGTGTGCTAGTACTTTTGTTGTTCGTTTATATGGAACGTTCAAG<br>GATGATTCAAATTTGTATTTTGTACTTGAATTAGCAGAACATGGTGACCTTGCAGAAGCC<br>GTAGGGGATATTGGAAGTCTTAACACTAATGTAGTTAAACTTCTTTCTGCTCAAATTTTT<br>GAAGCAATCTGTGTATGTCATAAAGCAAATGTTATCCATCGTGACCTCAAGCCAGAAAAC<br>ATTCTCCTCGACTCGCAAAACCACGTTCTTCTCTCAGATTTTGGTACAGCCCTAATTGAA<br>AAATCTGATAGTCAAGAATTAAATCGTTCATCCATTGTTGAACTCCAGCCTTTGTTGCCC<br>CAGAGCTCCTTAATGATGGAAAAATCTGTTATAGTTCTGATATGTGGTCATTTGGTTGTG<br>TCATATTCAATCTTCTTACAGGCACAGCACCTTTTAGTGGACAAAACACAGTTGAATTAA |

TABLE 1-continued lists *H. meleagridis* sequences found in the course of the present invention:

| SEQ ID NO | description | sequence |
| --- | --- | --- |
| 15 | sequence of attenuated strain contained in PCR product of primers with SEQ. ID NOs: 9 and 10 | ATTTGATAATAGTTTTTATTGGAGAAAATGTGGAAAGAATTGGAACTTCTGCATTTTCAT<br>ATTGCACATCATTAATAAATATTACAATTCCCAATAAAGTAACAGAAATTGGAAATTATG<br>TATTTTCATCATGTTCTAATTTGAGAATAGTTTTTATTGGAGAAAATGTGGAAAGAATTG<br>GAACTTATGCATTTTCATATTGCACATCATTAGTAAATATTACAATTCCCAATAAAGTAA<br>CAGGAATTGGAATTTCTTCATTTGAATTTTGTACCAACCTTCAAATGATTAAAGTTTCCA<br>GCGAAAATGCAAATTATTGCAATTATAACGAAGATGGGATTTTATATAACAAAAACGTCA<br>CTAAAATCCCACCGACGCAATCGTTCACACGATCGAACACATACTCAAACACATTTACTC<br>AGTCGAATACGTTCACTAAGTCGAATACATTCACTAAGACGAATACATTTACTCAGTCGA<br>ATACATTATTACCTTCGAATGTAACGCTGACACTTTCGTTTACGAATTCATATTCCATCA<br>CTGAAACTGTTACAATTTCTGGTACATATTCTTATTCATATGTTTTGACTTTAATTGGAG<br>TTAGTAGTACATATGTCAGAACAGATTTAATTTATTATGAATATATTGTGACTCGTTATT<br>CGACGTTATATAGTTTTTATTCGAATTTCTTCACAATTATCGACGTCATAAATCCTGTTG<br>GAAATGGTATTTCTCAAAAGGCTTTGATAGGTATTATCTGCGGCACAATAATTGCAGTTT<br>TGCTGATTATGGGAATTATCATATTCCTTGTGAAGAAATCAAAGAAAAGTAACAGCGAAT<br>CAACAGCGATAAAATTCGAAACTAAAAATTCAACTGGAAGCGATATGAGATCAGATGAAG<br>TAAATCAGGAATATAATGAACTCGTGTTGGAAGACCAG |
| 16 | sequence of attenuated strain contained in PCR product of primers with SEQ. ID NOs: 11 and 12 | CATCAAACTTAACCTTACTCAGTATCGCTGACAATGAAATATGGAGTGAAGGGACAAATA<br>ATATCATTAAAGCTGTTCGAGGTAGTACTATCACTGCATTAGATTTAAGTTATAACGTGG<br>TTGACTTAAAAAACCTCACTAGCTTGTTGGTAGATTTTGATAACATACAAGCCATTAGTA<br>TCAGTGGATGTAAAGTTTCTGAAAAAGATTTTCCAACTTTTATTTCGTCACTTCCAAAAA<br>CAAAATTAAGAACTCTTATCTTGGAAAGCCTTAATTTCCAACCTATTCCAATCTCTTGAC<br>CCGAAGTTCCTGATACCTTATGGACAACATATTTTGATATCTTTTTATCATCTTTATCAG<br>AATTCCAAACGATAGAAGATCTTCGACTTGGCTTTATGAATCTAGATCAACTTTATAAAG<br>TCAAGTCAACTCTTGAAAGACT |
| 17 | sequence of attenuated strain contained in PCR product of primers with SEQ ID NOs: 13 and 14 | CGTTCTTCTCTCAGATTTTGGTACAGCCCTAATTGAAAAATCTGATAGTCAAGAATTAAA<br>TCGTTCATCCATTGTTGAACTCCAGCCTTTGTTGCCCCAGAGCTCCTTAATGATGGAAAA<br>ATCTGTTATAGTTCTGATATGTGGTCATTTGGTTGTGTCATATTCAATCTTCTTACAGGC<br>ACAGCACCTTTTAGTGGACAAAACACAGTTGAATTAATGAACAACATCACTGAGCTTAAG<br>TTTAATCCAGTCATTAAAACACTTCCGAAAACCGCCAAAGATCTCATCACATCCTTACTT<br>AAGCTTGATCCACACGAGCGTATTGGATACGGGGAAGCCAAAG |

TABLE 2 lists primers and probes used:

| PCR assay | Sequence (5'-3') | Ta | product size | purpose |
| --- | --- | --- | --- | --- |
| indel: AGC Kinase | Forward AAATGTTATCCATCGTGACCTC (SEQ ID NO: 13)<br>Reverse GATAGCCTTCTTTGGCTTCC (SEQ ID NO: 14) | 52° C. | 409 bp | verification of indel |
| SNP: LRR | Forward TTGATTATGGGGCAACAGAAG (SEQ ID NO: 11)<br>Reverse TTGGCGAAGTCTTTCAAGAG (SEQ ID NO: 12) | 51° C. | 488 bp | verification of SNP |
| deletion $g6116_{vir}$ conventional PCR | Forward AGGATGTTTCAATTTCCTCGC (SEQ ID NO: 7)<br>Reverse CGGTTGTCCATTTTTCAAACAG (SEQ ID NO: 8) | 52° C. | 910 bp | verification of $g6116_{vir}$ deletion |
| deletion $g6116_{vir}$ qPCR | Forward TTTCAATTTCCTCGCCGCC (SEQ ID NO: 18)<br>Reverse CGCAAGACCAGCCAATATAAAC (SEQ ID NO: 19)<br>Probe HEX-TCGCCGCCGCCGCCTTCT-BHQ (SEQ ID NO: 20) | n/a | n/a | |

TABLE 2-continued

| lists primers and probes used: | | | | |
|---|---|---|---|---|
| PCR assay | Sequence (5'-3') | Ta | product size | purpose |
| deletion g7085$_{vir}$ conventional PCR | Forward GCGGGAAAACAAACGAAAC (SEQ ID NO: 9) Reverse ATAGCCATTGGTCCTGGTC (SEQ ID NO: 10) | 51° C. | 894 bp | verification of g7085$_{vir}$ deletion |
| deletion g7085$_{vir}$ qPCR | Forward ACATTCCCAACAAATGCCAG (SEQ ID NO: 21) Reverse GTGGGAGACATTCATCAATGAC (SEQ ID NO: 22) Probe FAM-CCAACGAATACATCGAATGTACCTGATGACAA-BHQ1 (SEQ ID NO: 23) | n/a | n/a | |

Further sequence information with respect to the attenuating features found in the course of the present invention:

(a)

g6116_vir is on contig_40_vir (SEQ ID NO: 24), on negative strand; coordinates of the gene:298557 . . . 301202. Coordinates of CDS: 298557 . . . 300901 and 300998 . . . 301202. Gene has one intron, coordinates of the intron: 300902 . . . 300997.

Corresponding locus is located on the contig_94_att (SEQ ID NO: 25), on the positive strand, coordinates: 243676 . . . 244657.

(b)

g7085_vir is on contig_51_vir (SEQ ID NO: 26), on negative strand; coordinates of the gene and CDS 528435 . . . 529427.

The corresponding locus in attenuated strain is located on contig_20_att (SEQ ID NO: 27) on positive strand with coordinates: 204754:205422.

(c)

g8794_vir is located on contig_72_vir (SEQ ID NO: 28), on positive strand; coordinates of the gene and CDS: 56499 . . . 58331

The corresponding locus in attenuated strain is g337_att. It is located on contig_106_att (SEQ ID NO: 29) on the negative strand, coordinates of the gene and CDS: 96062 . . . 96859.

(d)

g8786_vir is located on contig_72_vir (SEQ ID NO: 28), on negative strand; coordinates of the gene and CDS: 35920 . . . 37131.

The corresponding locus in attenuated strain is g346_att located on contig_106_att (SEQ ID NO: 29) on the positive strand; coordinates of the gene and CDS: 116227 . . . 116886.

RESULTS

Genome Assembly and Annotation

The whole genomes of two *H. meleagridis* strains—a virulent and an attenuated strain—were sequenced and annotated with the goals of expanding genomic information on this important poultry pathogen and investigating the genomic basis of attenuation. The strains used for whole genome sequencing originated from a single parasitic cell that was transferred via micromanipulation from the initial culture into the fresh suitable medium, establishing a so called "mono-eukaryotic clonal culture". Further prolonged in vitro cultivation resulted in the attenuation of the parasite. As aliquots of every cultivation passage were cryopreserved, retracement to the original virulent *H. meleagridis* was possible.

In order to achieve megabase-sized contigs with high base-level accuracy, the genomes of both strains were assembled using a combination of ONT long reads and Illumina short reads. The genome of *H. meleagridis* is 43 Mb in size, is GC poor (28%) and contains about ~11,000 genes, with little variation between strains. Introns are scarce, with 5.2-5.7% of genes containing at maximum one intron. Repetitive regions account for about ~2% of the genome in both strains and include microsatellites (1.63-1.75%), low complexity sequences (0.51-0.53%) and different classes of transposable elements. The overall genome duplication level in *H. meleagridis* was computed directly as the fraction of the genome that is duplicated instead of inferring this figure by indirect methods (i.e. Manekar & Sathe, 2019). To calculate this, the contigs were aligned to themselves with nucmer and extracted homologous regions with the show-coords tool (Marcais et al, 2018). This resulted in a duplication level of 20% for both strains. To evaluate the accuracy of the assemblies three metrics were employed: i) base-level accuracy, ii) presence of eukaryotic core genes and iii) completeness of gene models. Base-level accuracy was computed by aligning the assembly of each strain to another assembly generated using only Illumina read and computing the average genome similarity with the dnadiff (Marcais et al, 2018) tool, based on the assumption that accuracy from Illumina reads is higher compared to the ONT reads (McNaughton et al., 2019). Using this approach, 99.82% accuracy for the virulent strain and 99.79% for the attenuated strain were obtained. Next, the percentage of eukaryotic core genes was computed from the CEGMA database using BLAST. Out of total 458 core genes 395 (86%) in the virulent strain were detected and 395 (86%) in the attenuated strain, with 100% overlap between the two datasets, which was in accordance with the high similarity in gene content between strains. Last, the completeness of gene models was evaluated by classifying the CDS into complete (having stop and start codon) or partial (having only stop or only start) and found that 100% of the genes have complete CDS in both strains, underlining the high quality of the assemblies. To get an overview of genomic rearrangements for both assemblies, the contigs were aligned from the virulent strain to the attenuated strain using MAUVE (Darling et al, 2004). The alignment shows high colinearity between the two strains, no genomic rearrangements within contigs and two inverted contigs in the attenuated strain (FIG. 1). Overall, higher genome fragmentation was observed for the attenuated strain, concordant with the higher number of contigs.

Differences in Gene Content Between Strains

In order to find strain-specific losses/deletions or gene duplications that have occurred during the prolonged passaging of *H. meleagridis*, gene content between the two sequenced strains was compared. For this analysis, the protein sequences of both strains were clustered using OMA (Altenhoff et al, 2019) to detect gene families. A total of 11,119 genes from the virulent strain and 11,137 genes from the attenuated strain were clustered into 10,063 gene families. From this dataset, 400 genes were extracted that were found only in the attenuated strain and 281 of them aligned to the virulent strain using Exonerate (Slater & Birney, 2005) (parameters-model protein2genome –percent 90–bestn 1), indicating that these genes simply represent missing annotations in the attenuated strain. Of the remaining 119 genes, five of them ($g8917^{att}$→$g8921_{att}$ on contig 49) had no support from Illumina reads in the virulent strain, pointing to a deletion in the virulent strain. As these genes did not have any marked functional annotation, additional BLAST searches were conducted, which revealed that these five genes belonged to a phage contamination located on a chimeric contig. Using the same approach, 335 genes were extracted that were found only in the virulent strain and found that 234 of them aligned the attenuated strain using Exonerate. Of the remaining 101 genes, 99 of them had full support from Illumina reads, indicating missing annotations, while two of them (g6116vir on contig 40 and g7085vir on contig 51) had only partial support from Illumina reads in the attenuated strain (FIG. 2*a*, FIG. 3*a*), pointing to a deletion that occurred in the attenuated strain. The g6116vir gene encodes for a hypothetical protein with transmembrane domain towards the C-terminus as identified by InterProScan (Quevillon et al, 2005) (FIG. 2*b*). The g7085vir encodes a leucine-rich repeat (LRR) domain-containing protein. As LRR proteins of the BspA family are involved in virulence in trichomonads (Handrich et al, 2019), the presence of BspA motifs in this protein was checked with the online tool MOTIF and a single BspA motif at positions 38→88 was identified (FIG. 3*b*). Additionally, the protein encoded by $g7085_{vir}$ also contains four predicted transmembrane helices (FIG. 3*c*).

Confirmation of Gene Deletions

In order to confirm deletions of $g6116_{vir}$ and $g7085_{vir}$ in the attenuated strain and narrow the time point, i.e. passage number, when the deletion occurred, a range of different passages was tested for the presence/absence of loci by conventional and real-time PCR. The $g6116_{vir}$ deletion was confirmed in the attenuated strain. The analysis showed that the deletion of the $g6116_{vir}$ occurred already in the xenic background between the passage 83 and 145. In addition, testing low and high passages of other unrelated *H. meleagridis* strains, grown as xenic clonal cultures, demonstrated that $g6116_{vir}$ did not change and remained as wild type throughout the in vitro cultivation.

Variants Identification Between Strains

Next, SNPs and indels between strains were analyzed to find variants affecting the coding regions (non-synonymous and missense mutations), as these are correlated with a change of gene function that occurred during the attenuation process. The critical step in this analysis is to distinguish true variants from sequencing errors introduced by the ONT reads (layer et al., 2015). After aligning the genome of the attenuated to the virulent strain with nucmer, an initial set of 17,170 SNPs was identified using the show-snps tool (Marcais et al, 2018). After removing sequencing errors (see Methods, Identification of variants between strains, above), a filtered set of 68 homozygous SNPs and 2933 heterozygous SNPs was obtained. Only homozygous SNPs were considered for the following analyses. Of the 68 homozygous SNPs, 17 were located within coding regions: of these, 4 were synonymous, 12 non-synonymous and 1 caused a premature stop codon in a protein of the attenuated strain ($g337_{att}$) (FIG. 4*a*). Using the local BLAST search against transcriptomes of virulent and attenuated strain (Mazumdar et al, 2017) it became evident that both strains express this gene, with the transcript from the attenuated gene displaying the SNP. Both versions, a complete ($g8794_{vir}$) and a truncated ($g337_{att}$) contain LRR_RI superfamily domain (sd00116) located in the N-terminal part, however the truncated version lacked the second LRR domain (LRR_AMN1 (sd00034)) (FIG. 4*a*). The characterization of the truncation with PROVEAN tool (Protein Variation Effect Analyzer) (Choi & Chan, 2015) marked the event as deleterious for the protein function. The remaining non-synonymous SNPs were also characterized with PROVEAN; 2 out of 12 were marked as deleterious, although both of them did not affect functional domains. Indels were detected from the alignment of the attenuated to the virulent strain using the show-snps tool (Marcais et al, 2018) with the indel option selected. The initial unfiltered set contained 21,822 indels. After extracting homozygous indels supported by the Illumina reads 2 true indels were obtained: the first was an insertion of an A located in a non-coding region: a microsatellite located at position $151{,}264_{vir}$ of contig 33, which was disregarded as common microsatellite variation. However, the second was a deletion of a G located in the coding region of gene $g346_{att}$ which generated a frameshift introducing a premature stop codon. Alignment of $g346_{att}$ together with the corresponding orthologs in the virulent strain ($g8786_{vir}$) and the other sequenced *Parabasalia* species confirmed that the truncation of $g346_{att}$ is specific to the attenuated strain (FIG. 4*b*). Both $g346_{att}$ and $g8786_{vir}$ encode for an AGC family protein kinase, as evident by the presence of a protein kinase ATP binding site and the serine/threonine kinase site in both coding sequences (FIG. 4*b*). However, due to the indel in $g346_{att}$ coding sequence, the pleckstrin homology domain located in the C-terminal part of $g8786_{vir}$ and other Parabasalid orthologues was lost in $g346_{att}$ (FIG. 4*b*). The PROVEAN tool characterization of the mutations that were caused by the frameshift, such as the exchange 38 amino acids and the truncation, labelled the indel event as deleterious for the protein. Interestingly, the complete exchange of the last 38 amino acids before the premature stop codon, produced a short transmembrane domain at the C-terminus of $g346_{att}$ (FIG. 4*b*). It turned out that neither of the strains expressed this gene during in vitro growth.

Confirmation of Variants

Similar to the confirmation of gene deletions, virulent and attenuated *H. meleagridis* strains from monoxenic cultivation were analyzed, which were used for NGS analysis, for the presence/absence of both truncating mutations, the SNP and the indel, by conventional PCR coupled with Sanger sequencing of PCR products. In order to narrow the timepoint in which the mutations occurred, a set of xenic cultures of different passages spanning the period during which the attenuation occurred was used for this analysis. Both truncating mutations could be confirmed in the attenuated strain grown as monoxenic culture, whereas the gene was intact in the virulent strain grown under same conditions. Moreover, the analysis showed that both the SNP and the indel already occurred in xenic conditions with the indel appearing between passage 83 and 145, and the SNP occurring later between passages 145 and 237.

Discussion

Comparison of the two *H. meleagridis* genomes (of the virulent and an attenuated strain, respectively) with each other showed that the gene content is very similar between the two strains, which was expected considering that the origin of both strains can be traced to a same parent cell. But it also singled out two coding regions that showed only partial support from Illumina reads in the attenuated strain. This indicated that during long term in vitro cultivation a deletion within these genes occurred in the virulent strain, which during this process became attenuated. In addition to confirming the g6116$_{vir}$ deletion independently in the attenuated strain, it was demonstrated that the deletion occurred already during in vitro cultivation in xenic conditions between passage 83 and 145, and not in the course of the monoxenization process through which both virulent and attenuated strains went independently. The gene g6116$_{vir}$ encodes for a hypothetical protein, however further BLAST searches revealed that the orthologue of g6116$_{vir}$ in *T. vaginalis* encodes for a putative cell-surface adhesin. The probable membrane association of g6116$_{vir}$ is supported by the presence of a transmembrane domain towards the C-terminus. This potential surface adhesin function and its loss in the attenuated strain speaks for its role in the virulence of the parasite. Aside from the role in virulence of *H. meleagridis*, the loss of protein encoded by g6116$_{vir}$ is supportive for the adaptation to the in vitro growth. Long-term cultivated parasites, which lack this gene, turned out to be much easier to cultivate and grow to much higher numbers in vitro than the parasites that were in culture for just few passages.

Further investigations on determining possible genes involved in the attenuation focused on the analysis of SNPs and indels between two genomes. A total of 13 homozygous nonsynonymous SNPs were detected in coding regions, with one of them resulting in the truncation of the protein in the attenuated strain due to the premature stop codon. The affected gene, g8794$_{vir}$/g337$_{att}$, encodes for LRR domain containing protein. As compared to its wild type partner in the virulent strain (g8794$_{vir}$), the g337$_{att}$ lacks a second LRR domain located at the C-terminus, and by that may represent a pseudogenization event. This mutation was identified by the PROVEAN software tool as deleterious.

The analysis identifying indels that modify coding regions detected a single event, which due to the frameshift introduced an exchange of 38 amino acids and a premature stop codon. The gene g8786$_{vir}$ and its counterpart in the attenuated strain (g346$_{att}$), encode a serine/threonine kinase as judged by the presence of the protein kinase ATP binding site and the serine/threonine kinase site in both coding sequences. However, due to the indel the g346$_{att}$ lacks a C-terminally located pleckstrin homology (PH) domain, which binds phosphoinositides and by that targets the protein to the cellular membrane. The frameshift that occurred in the mutated g346$_{att}$ changed the last 38 amino acids, that now are predicted to form a short transmembrane domain at the C-terminus. The functionality prediction by PROVEAN tool characterized the mutant as deleterious. The fact that its transcript could not be detected in the transcriptome of the in vitro grown parasites indicates that g8786$_{vir}$/g346$_{att}$ might only be expressed in vivo, during the infection of the host. Expression during infection of the host is typical for virulence factors.

In conclusion, combining the sequence data from two conceptually different sequencing platforms: Nanopore long reads and Illumina short reads enabled us to assemble high-quality genome sequences from two phenotypically different *H. meleagridis* strains, a parasite with limited sequence data available so far. Two gene deletions and two gene truncations differing between virulent and attenuated strain were found, as disclosed above.

Example 2

Application of the Inventive Vaccine

An *H. meleagridis* strain having all of attenuating features (a)-(d) disclosed hereinabove is cultivated with a single bacterial strain (namely an *E. coli* strain). The cells are pelleted and washed in phosphate-buffered saline. Then, phosphate-buffered saline with guar gum as a thickener is added. Thereby, a live *H. meleagridis* vaccine with a bacterial component is obtained.

This vaccine is administered orally (at about $1\times10^5$ *H. meleagridis* cells per dose) to 30 one-day-old turkeys (Converter, Hybrid Europe, Malguénac, France). Feed (commercial turkey starter feed) and water are provided ad libitum, except for a 5-hour period of feed restriction immediately after administration.

NON-PATENT REFERENCES

Altenhoff A M, Levy J, Zarowiecki M, Tomiczek B, Warwick V A, Dalquen D A, Muller S, Telford M J, Glover N M, Dylus D, Dessimoz C (2019) OMA standalone: orthology inference among public and custom genomes and transcriptomes. Genome Res 29: 1152-1163.

Bilic, Ivana, and Michael Hess. "Interplay between *Histomonas meleagridis* and Bacteria: Mutualistic or Predator-Prey?." Trends in parasitology 36.3 (2020): 232-235.

Brás, Xavier Pereira, et al. "Knockout of the abundant *Trichomonas vaginalis* hydrogenosomal membrane protein TvHMP23 increases hydrogenosome size but induces no compensatory up-regulation of paralogous copies." FEBS letters 587.9 (2013): 1333-1339.

Choi Y, Chan A P (2015) PROVEAN web server: a tool to predict the functional effect of amino acid substitutions and indels. Bioinformatics 31: 2745-2747.

Clark S, Kimminau E (2017) Critical Review: Future Control of Blackhead Disease (Histomoniasis) in Poultry. Avian Dis 61: 281-288.

Darling A C, Mau B, Blattner F R, Perna N T (2004) Mauve: multiple alignment of conserved genomic sequence with rearrangements. Genome Res 14: 1394-1403.

Ganas P, Liebhart D, Glosmann M, Hess C, Hess M (2012) *Escherichia coli* strongly supports the growth of *Histomonas meleagridis*, in a monoxenic culture, without influence on its pathogenicity. Int J Parasitol 42: 893-901.

Handrich M R, Garg S G, Sommerville E W, Hirt R P, Gould S B (2019) Characterization of the BspA and Pmp protein family of trichomonads. Parasit Vectors 12: 406.

Hess M, Kolbe T, Grabensteiner E, Prosl H (2006) Clonal cultures of *Histomonas meleagridis, Tetratrichomonas gallinarum* and a *Blastocystis* sp. established through micromanipulation. Parasitology 133: 547-554.

Hess M, Liebhart D, Grabensteiner E, Singh A (2008) Cloned *Histomonas meleagridis* passaged in vitro resulted in reduced pathogenicity and is capable of protecting turkeys from histomonosis. Vaccine 26: 4187-4193

Hess M, Liebhart D, Bilic I, Ganas P (2015) Histomonas meleagridis—New insights into an old pathogen. Vet Parasitol 208: 67-76.

Hoff K J, Stanke M (2013) WebAUGUSTUS—a web service for training AUGUSTUS and predicting genes in eukaryotes. Nucleic Acids Res 41: W123-W128.

Janssen, Brian D., et al. "CRISPR/Cas9-mediated gene modification and gene knock out in the human-infective parasite *Trichomonas vaginalis*." Scientific reports 8.1 (2018): 1-14.

Land, Kirkwood M., et al. "Targeted gene replacement of a ferredoxin gene in *Trichomonas vaginalis* does not lead to metronidazole resistance." Molecular microbiology 51.1 (2004): 115-122.

layer T, Harrison J, O'Neill P A, Moore K, Farbos A, Paszkiewicz K, Studholme D J (2015) Assessing the performance of the Oxford Nanopore Technologies MinION. Biomol Detect Quantif 3: 1-8.

Liebhart D, Ganas P, Sulejmanovic T, Hess M (2017) Histomonosis in poultry: previous and current strategies for prevention and therapy. Avian Pathol 46: 1-18

Manekar S C, Sathe S R (2019) Estimating the k-mer Coverage Frequencies in Genomic Datasets: A Comparative Assessment of the State-of-the-art. Curr Genomics 20: 2-15.

Marcais G, Delcher A L, Phillippy A M, Coston R, Salzberg S L, Zimin A (2018) MUMmer4: A fast and versatile genome alignment system. PLoS Comput Biol 14: e1005944.

Mazumdar R, Endler L, Monoyios A, Hess M, Bilic I (2017) Establishment of a de novo Reference Transcriptome of *Histomonas meleagridis* Reveals Basic Insights About Biological Functions and Potential Pathogenic Mechanisms of the Parasite. Protist 168: 663-685.

Mazumdar R, Nobauer K, Hummel K, Hess M, Bilic I (2019) Molecular characterization of *Histomonas meleagridis* exoproteome with emphasis on protease secretion and parasite-bacteria interaction. PLoS One 14: e0212429.

McNaughton A L, Roberts H E, Bonsall D, de C M, Mokaya J, Lumley S F, Golubchik T, Piazza P, Martin J B, de L C, Brown A, Ansari M A, Bowden R, Barnes E, Matthews P C (2019) Illumina and Nanopore methods for whole genome sequencing of hepatitis B virus (HBV). Sci Rep 9: 7081.

Molgora, Brenda M., et al. "A Novel *Trichomonas vaginalis* Surface Protein Modulates Parasite Attachment via Protein: Host Cell Proteoglycan Interaction." Mbio 12.1 (2021).

Monoyios A, Patzl M, Schlosser S, Hess M, Bilic I (2017) Unravelling the differences: comparative proteomic analysis of a clonal virulent and an attenuated *Histomonas meleagridis* strain. Int J Parasitol.

Monoyios A, Hummel K, Nobauer K, Patzl M, Schlosser S, Hess M, Bilic I (2018) An Alliance of Gel-Based and Gel-Free Proteomic Techniques Displays Substantial Insight Into the Proteome of a Virulent and an Attenuated Histomonas meleagridis Strain. Front Cell Infect Microbiol 8: 407.

Mazumdar R, Nobauer K, Hummel K, Hess M, Bilic I (2019) Molecular characterization of *Histomonas meleagridis* exoproteome with emphasis on protease secretion and parasite-bacteria interaction. PLoS One 14: e0212429.

McDougald, L. R. "Blackhead disease (histomoniasis) in poultry: a critical review." Avian diseases 49.4 (2005): 462-476.

McDougald L R, Fuller L (2005) Blackhead disease in turkeys: direct transmission of *Histomonas meleagridis* from bird to bird in a laboratory model. Avian Dis 49: 328-331.

Langmead B, Salzberg S L (2012) Fast gapped-read alignment with Bowtie 2. Nat Methods 9: 357-359.

Li H (2018) Minimap2: pairwise alignment for nucleotide sequences. Bioinformatics 34: 3094-3100.

Nicholls S M, Quick J C, Tang S, Loman N J (2019) Ultra-deep, long-read nanopore sequencing of mock microbial community standards. Gigascience 8. 5486468.

Quevillon E, Silventoinen V, Pillai S, Harte N, Mulder N, Apweiler R, Lopez R (2005) InterProScan: protein domains identifier. Nucleic Acids Res 33: W116-W120.

Slater G S, Birney E (2005) Automated generation of heuristics for biological sequence comparison. BMC Bioinformatics 6: 31.

Smit A, Hubley R, Green P (2013) RepeatMasker Open-4.0.

Stanke M, Keller O, Gunduz I, Hayes A, Waack S, Morgenstern B (2006) AUGUSTUS: ab initio prediction of alternative transcripts. Nucleic Acids Res 34: W435-W439.

Vaser R, Sovic I, Nagarajan N, Sikic M (2017) Fast and accurate de novo genome assembly from long uncorrected reads. Genome Res 27: 737-746.

---

SEQUENCE LISTING

The patent contains a lengthy sequence listing. A copy of the sequence listing is available in electronic form from the USPTO web site (https://seqdata.uspto.gov/?pageRequest=docDetail&DocID=US12098361B2). An electronic copy of the sequence listing will also be available from the USPTO upon request and payment of the fee set forth in 37 CFR 1.19(b)(3).

---

We claim:

1. A *Histomonas meleagridis* strain having all of the following attenuating features:

(a) an inactivation of a gene, wherein the gene has the sequence identified by SEQ ID NO: 1 or a sequence with at least 90% sequence identity thereto, (b) an inactivation of a gene, wherein the gene has the sequence identified by SEQ ID NO: 2 or a sequence with at least 90% sequence identity thereto, (c) a truncating mutation in the coding sequence of a gene, wherein the gene has the unmutated coding sequence identified by SEQ ID NO: 3 or an unmutated coding sequence with at least 95% sequence identity thereto, and (d) a truncating mutation in the coding sequence of a gene, wherein the gene has the unmutated coding sequence identified by SEQ ID NO: 4 or an unmutated coding sequence with at least 95% sequence identity thereto.

2. The strain of claim 1, wherein at least one attenuating feature is a homozygous feature.

3. The strain of claim 1, wherein the inactivation of the gene is a deletion.

4. The strain of claim 1, wherein the truncating mutation is a frameshift mutation or a point mutation leading to a premature stop codon.

5. The strain of claim 1, wherein the gene with the truncating mutation of attenuating feature (c) has the coding sequence identified by SEQ ID NO: 5 or a coding sequence with at least 95% sequence identity thereto.

6. The strain of claim 1, wherein the gene with the truncating mutation of attenuating feature (d) has the coding sequence identified by SEQ ID NO: 6 or a coding sequence with at least 95% _sequence identity thereto.

7. The strain of claim 1, wherein the strain has attenuating feature (a), wherein a genomic PCR of the strain with forward primer AGGATGTTTCAATTTCCTCGC (SEQ ID NO: 7) and reverse primer CGGTTGTCCATTTTT-CAAACAG (SEQ ID NO: 8) does not yield a product.

8. The strain of claim 1, wherein the strain has attenuating feature (b), wherein a genomic PCR of the strain with forward primer GCGGGAAAACAAACGAAAC (SEQ ID NO: 9) and reverse primer ATAGCCATTGGTCCTGGTC (SEQ ID NO: 10) yields a product with a size between 850 bp to 950 bp comprising the sequence identified by SEQ ID NO: 15 or a sequence with at least 90% sequence identity thereto.

9. The strain of claim 1, wherein the strain has attenuating feature (c), wherein a genomic PCR of the strain with forward primer TTGATTATGGGGCAACAGAAG (SEQ ID NO: 11) and reverse primer TTGGCGAAGTCTTT-CAAGAG (SEQ ID NO: 12) yields a product with a size between 450 bp to 550 bp comprising the sequence identified by SEQ ID NO: 16.

10. The strain of claim 1, wherein the strain has attenuating feature (d), wherein a genomic PCR of the strain with forward primer AAATGTTATCCATCGTGACCTC (SEQ ID NO: 13) and reverse primer GATAGCCTTCTTTGGCTTCC (SEQ ID NO: 14) yields a product with a size between 350 bp to 450 bp comprising the sequence identified by SEQ ID NO: 17.

11. A *Histomonas meleagridis* strain having four attenuating features verifiable by:

(a) a genomic PCR of the strain with forward primer AGGATGTTTCAATTTCCTCGC (SEQ ID NO: 7) and reverse primer CGGTTGTCCATTTTT-CAAACAG ((SEQ ID NO: 8) not yielding a product, (b) a genomic PCR of the strain with forward primer GCGGGAAAACAAACGAAAC (SEQ ID NO: 9) and reverse primer ATAGCCATTGGTCCTGGTC (SEQ ID NO: 10) yielding a product with a size between 850 bp to 950 bp comprising the sequence identified by SEQ ID NO: 15 or a sequence with at least 90% sequence identity thereto, (c) a genomic PCR of the strain with forward primer TTGATTATGGGGCAACAGAAG (SEQ ID NO: 11) and reverse primer TTGGCGAAGTCTTTCAAGAG (SEQ ID NO: 12) yielding a product with a size between 450 bp to 550 bp comprising the sequence identified by SEQ ID NO: 16, or (d) a genomic PCR of the strain with forward primer AAATGTTATCCATCGTGACCTC (SEQ ID NO: 13) and reverse primer GATAGCCTTCTTTGGCTTCC (SEQ ID NO: 14) yielding a product with a size between 350 bp to 450 bp comprising the sequence identified by SEQ ID NO: 17.

12. A method of attenuating *Histomonas meleagridis*, comprising the steps of obtaining *Histomonas meleagridis* cells; and introducing at least all of the following attenuating features:

(a) an inactivation of a gene, wherein the gene has the sequence identified by SEQ ID NO: 1 or a sequence with at least 90% sequence identity thereto, (b) an inactivation of a gene, wherein the gene has the sequence identified by SEQ ID NO: 2 or a sequence with at least 90% sequence identity thereto, (c) a truncating mutation in the coding sequence of a gene, wherein the gene has the unmutated coding sequence identified by SEQ ID NO: 3 or an unmutated coding sequence with at least 95% sequence identity thereto, and (d) a truncating mutation in the coding sequence of a gene, wherein the gene has the unmutated coding sequence identified by SEQ ID NO: 4 or an unmutated coding sequence with at least 95% sequence identity thereto, into at least one of the *Histomonas meleagridis* cells.

13. A *Histomonas meleagridis* cell, obtainable by the method of claim 12.

14. A vaccine comprising cells of the strain of claim 1, wherein the cells are live or inactivated, and at least one pharmaceutically acceptable excipient.

15. The vaccine of claim 14, wherein the vaccine is further defined as a live vaccine.

16. The vaccine of claim 14, wherein the vaccine is formulated as a gel.

17. The vaccine of claim 14, wherein the vaccine is suitable for prevention of histomonosis.

18. The method of claim 12, wherein the method produces the *Histomonas meleagridis* of claim 1.

19. The strain of claim 3, wherein the inactivation deletion of the gene is a full deletion of the gene.

* * * * *